(12) United States Patent
Billhardt et al.

(10) Patent No.: US 6,369,057 B1
(45) Date of Patent: *Apr. 9, 2002

(54) QUINOXALINES, PROCESSES FOR THEIR PREPARATION AND THEIR USE

(75) Inventors: Uta-Maria Billhardt, Kronberg/Taunus; Manfred Rösner, Eppstein/Taunus; Günther Riess, Hattersheim am Main; Irvin Winkler, Liederbach; Rudolf Bender, Bad Soden am Taunus, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/418,896

(22) Filed: Apr. 7, 1995

Related U.S. Application Data

(63) Continuation of application No. 08/140,896, filed on Oct. 25, 1993, now abandoned, which is a continuation-in-part of application No. 07/867,512, filed on Apr. 13, 1992, now abandoned.

(30) Foreign Application Priority Data

Apr. 15, 1991 (DE) ............................................. 41 12234
Dec. 20, 1991 (DE) ............................................. 41 42322

(51) Int. Cl.$^7$ .................. A61K 31/498; A61K 31/5377; C07D 241/44; C07D 413/10

(52) U.S. Cl. ................. 514/234.8; 514/249; 514/228.2; 544/6; 544/62; 544/70; 544/116; 544/119; 544/231; 544/354

(58) Field of Search ................................ 544/354, 231, 544/116, 119, 70, 6, 62; 514/228.2, 234.8, 249

(56) References Cited

U.S. PATENT DOCUMENTS

| | | | | |
|---|---|---|---|---|
| 3,479,348 A | * | 11/1969 | Yamamoto et al. | 544/354 |
| 3,654,275 A | | 4/1972 | McManus | 544/354 |
| 4,032,639 A | | 6/1977 | Freed et al. | 514/250 |
| 4,203,987 A | | 5/1980 | Freed | 514/250 |
| 4,940,708 A | | 7/1990 | Sarges | 514/249 |
| 5,723,461 A | * | 3/1998 | Rösner et al. | 514/249 |

FOREIGN PATENT DOCUMENTS

| | | | |
|---|---|---|---|
| AT | 28 48 48 | 9/1970 | |
| BE | 706 623 | 11/1967 | |
| CA | A-1278695 | 1/1991 | |
| EP | A-0190105 | 8/1986 | ................. 514/249 |
| EP | 0266102 | 5/1988 | |
| JP | 4417137 | * 7/1969 | |
| JP | 45-8422 | * 3/1970 | |

OTHER PUBLICATIONS

Yamamoto *Chemical Abstracts*, vol. 71, No. 124490v (Abstract for JP 69 17,137, Jul. 29, 1969).*

Yamamoto et al *Chemical Abstracts*, vol. 73, No. 14873f (Abstract for JP 70 08422, Mar. 26, 1970).*

Hinsberg, *Justus Liebig's Annalen Der Chemie*, 248, p71–84 (1888).*

Bird, *J. Chem. Soc.*, p674–677 (1963).*

Otomasu et al, *Chemical Abstracts*, vol. 78, No. 136218 (1973).*

Kalyanam et al, *Chemical Abstracts*, vol. 116, No. 83647 (1992).*

Mansuri et al, *Chemtech*, pp564–572 (Sep. 1992).*

Saunders, *Drug Design and Discovery*, 8, pp255–263 (1992).*

Abstract for JP 17136/69 (Jul. 29, 1969).

Abstract for JP 17137/69 (Jul. 29, 1969).

Robert Ning et al., Quinazolines and 1,4–benzodiazepines, XLVI. Photochemistry of nitrones and oxaziridines, J. Heterocycl. Chem. (1970), 7(3), 475–8 (online printout of compounds).

R. Ian Fryer et al., Synthesis of amidines from cyclic amides, J. Org. Chem. (1969), 34 (4), 1143–5 (Online printout of compounds).

A. Mederos et al., Polyaminocarboxylic acids with quinoxaline structure derived from o–diamines, An. Quim., Ser. B (1983), 79(3), 328–35 (Online prinout of compounds).

(List continued on next page.)

*Primary Examiner*—Emily Bernhardt
(74) *Attorney, Agent, or Firm*—Finnegan, Henderson, Farabow, Garrett and Dunner, L.L.P.

(57) ABSTRACT

Compounds of the formula I or Ia

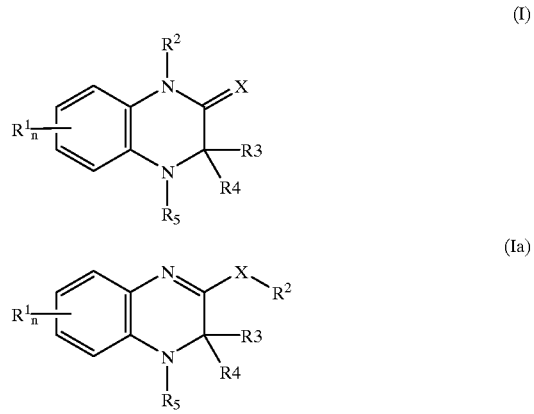

in which n and the substituents $R^1$, $R^5$ and x have the meaning mentioned have an antiviral activity.

6 Claims, No Drawings

OTHER PUBLICATIONS

N. Borthakur et al., Studies in 1,2,3,4–tetrahydro–3–oxoquinoxaline–1–acetic acid: a facile oxidation of active methylene group, Indian J. Chem., Sect. B (1981), 20B(9), 822–4 (online printout of compounds).

Sumitomo Chem. Co., BE706,623 (1.4.68) Quinoxalinones: Anti–Inflammatory, Analgesic Antipyretic.

Sankyo Co. Ltd., JA–7038639–R (05.12.70), Suspension for Ming Tablets Prodn. . . (abstract).

Sumitomo Chem. Co. Ltd., JA–7038700–R (07.12.70), Novel 4–Acyl–3,4–Dihydro–2(1H)Quinoxaline Derivs Having Antinflammatory Antipyretic and Analgesic Activity (Abstract).

Sankyo Co., JA–7035800–R (14.11.70), Coating Base Contg Polyvinylacetaldiethyl–Amino Acetate (Abstract).

Takeda Chem. Ind. Ltd., JA–7035881–R (16.11.70); Pelletization Process. . . (Abstract).

Sumitomo Chem. Co. Ltd., JA–7035903–R (16.11.70); 4–Phenyl(Or Furyl)–Alkan (OR E)–Oyl–3,4Dihydro–Quinoxaline–2–Ones, Antifebrile, Anodyne (Abstract).

Sumitomo Chem. Ind. Co. Ltd., JA–30509/69 (11–4–66); (JA) as 23097/66 (9.12.69), 4–Thienoyl–6(OR 7)–Alkoxy–3,4–Dihydro–2[1H]–Quinoxalin–2–Ones Antiphlogistic, Antiferbrile, Analgesic (Abstract).

EP 315959A; Novel quinoxaline derivs. useful as neurotropic agents (Abstract).

U.S. 3,697,545 (10.10.72); 9–Chloro–5–methylamino–2–phenyl–4H–1,3,6–benzoxadiazocine,–antiinflammatory, anticonvulsant, and antibacterial agent (Abstract).

Hirotaka Otomasu et al., "A New Synthesis of 5,6–Dihydro–4H–imidazo[1,5,4–d,e]quinoxaline–5–ones," Chem. Pharm. Bull., 21[2], (1973), pp. 353–357.

T.O. Olagbemiro et al., "Synthesis and Reactions of 3–Phenyl–3,4–Dihydro–1,4–Quinoxalin–2(1H)–One and its Heterocyclic Analogues," Bull. Soc. Chim. Belg., 96[6], (1987), pp. 473–480.

\* cited by examiner

QUINOXALINES, PROCESSES FOR THEIR PREPARATION AND THEIR USE

This application is a continuation of prior application Ser. No. 08/140,896 filed Oct. 25, 1993, now abandoned, which was a continuation of prior application Ser. No. 07/867,512 filed Apr. 13, 1992, abandoned.

The present invention relates to quinoxalines, to processes for their preparation, and to their use.

Quinoxalines are a well-known class of compound (O. Hinsberg, J. Liebigs Ann. Chem. 237, 327 (1986)).

Quinoxaline derivatives have been described in the patent literature for use in various applications in medicine. Austrian Patent 284,848 (19.12.67) mentions 1-N-dialkylaminoalkyl-3,4-dihydroquinoxalin-2(1H)-ones as spasmolytic agents. A series of patent applications by the Japanese company Sumitomo Chem. Co. Ltd. describe 4-N-aroyl-, arylacyl- and arylsulfonyl-3,4-dihydroquinoxalin-2(1H)-ones which have an antiinflammatory action (JA 17,137/69 (11.4.66), JA 17,136/69 (8.4.66), JA 7,008/422 (9.8.66), BE 706,623 (16.11.66)). 3,4-Dihydroquinoxalin-2(1H)-one-3-carboxamides are contained in U.S. Pat. No. 3,654,275 (4.4.72). They, too, have an antiinflammatory action. In U.S. Applications U.S. Pat. Nos. 4,203,987 (21.5.79) and 4,032,639 (22.3.76), pyridinyl-alkyltetrahydropyrazino[1,2-a]quinoxalinone derivatives are described by American Home Prod. Corp. as antihypertensive and antisecretory reagents. A European Patent Application by Pfizer Inc. (EP 266,102 A (30.10.86)) includes 4-N-benzenesulfonyl-3,4-dihydroquinoxalin-2 (1H)-one-1-alkylcarboxylic acids as aldose reductase inhibitors. However, an antiviral activity has not been demonstrated to date.

Surprisingly, it has now been found that quinoxalines of the formulae I and Ia

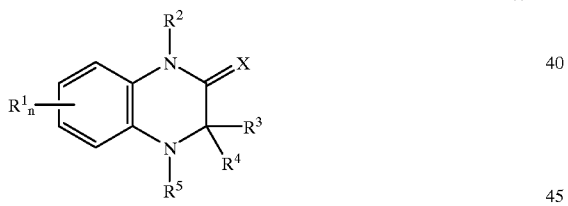

(I)

and their tautomeric forms of the formula Ia

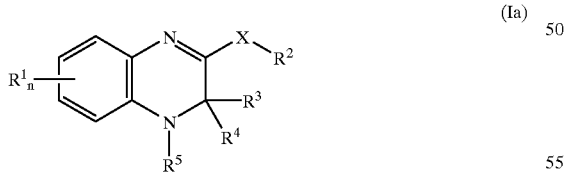

(Ia)

and physiologically acceptable salts or prodrugs thereof have an antiviral action, in particular against retroviruses, for example against the human immunodeficiency virus (HIV).

In the compounds of the formula I or Ia according to the invention, 1) n is
   zero,
   one,
   two,
   three
   or four, the individual substituents $R^1$ independently of one another are
   fluorine, chlorine, bromine, iodine, trifluoromethyl, trifluoromethoxy, hydroxyl, $C_1$–$C_8$-alkyl, $C_5$–$C_8$-cycloalkyl, $C_1$–$C_6$-alkoxy, ($C_1$–$C_6$-alkoxy)-($C_1$–$C_4$-alkoxy), $C_1$–$C_6$-alkylthio, $C_1$–$C_6$-alkylsulfinyl, $C_1$–$C_6$-alkylsulfonyl, nitro, amino, azido, $C_1$–$C_6$-alkylamino, di($C_1$–$C_6$-alkyl)amino, piperidino, morpholino, 1-pyrrolidinyl, 4-methylpiperazinyl, thiomorpholino, imidazolyl, triazolyl, tetrazolyl, $C_1$–$C_6$-acyl, $C_1$–$C_6$-acyloxy, $C_1$–$C_6$-acylamino, cyano, carbamoyl, carboxyl, ($C_1$–$C_6$-alkyl)oxycarbonyl, hydroxysulfonyl, sulfamoyl or
   a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, 2-pyridyl, 3-pyridyl or 4-pyridyl radical which is substituted by up to five radicals $R^6$ which are independent of one another,
   where $R^6$ can be fluorine, chlorine, bromine, iodine, cyano, trifluoromethyl, trifluoromethoxy, nitro, amino, azido, $C_1$–$C_6$-alkyl, $C_3$–$C_8$-cycloalkyl, $C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylamino, di($C_1$–$C_6$-alkyl) amino, ($C_1$–$C_6$-alkyl)oxycarbonyl, phenyl, phenoxy, 2-, 3- or 4-pyridyl, $R^2$ is hydrogen, $C_1$–$C_6$-alkoxy, hydroxyl, picolyl, cyclopropyl or isopropenyloxycarbonyl and $R^5$ is
   hydrogen, hydroxyl, $C_1$–$C_6$-alkoxy, aryloxy, $C_1$–$C_6$-acyloxy, cyano, amino, $C_1$–$C_6$-alkylamino, di($C_1$–$C_6$-alkyl)amino, arylamino, $C_1$–$C_6$-acylamino, $C_1$–$C_8$-alkyl, optionally substituted by
      fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
   $C_2$–$C_8$-alkenyl,
   optionally substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl and carbamoyl;
   $C_3$–$C_8$-allenyl, optionally substituted by fluorine, chlorine or hydroxyl,
   $C_1$–$C_4$-alkoxy, oxo, phenyl;
   $C_3$–$C_8$-alkynyl,
   optionally substituted by
      fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
   $C_3$–$C_8$-cycloalkyl,
   optionally substituted by
      fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_3$–$C_8$-cycloalkenyl,
optionally substituted by
   fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
($C_3$–$C_8$-cycloalkyl)-($C_1$–$C_4$-alkyl),
optionally substituted by
   fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
($C_3$–$C_8$-cycloalkenyl)-($C_1$–$C_4$-alkyl),
optionally substituted by
   fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
$C_1$–$C_6$-alkylcarbonyl,
optionally substituted by
   fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
$C_2$–$C_8$-alkenylcarbonyl, optionally substituted by fluorine, chlorine or hydroxyl, $C_1$–$C_4$-alkoxy, oxo, phenyl;
($C_3$–$C_8$-cycloalkyl)carbonyl, optionally substituted by fluorine, chlorine or hydroxyl, $C_1$–$C_4$-alkoxy, oxo, phenyl;
($C_5$–$C_8$-cycloalkenyl)carbonyl, optionally substituted by fluorine, chlorine or hydroxyl, $C_1$–$C_4$-alkoxy, oxo, phenyl;
($C_3$–$C_8$-cycloalkyl)-($C_1$–$C_3$-alkyl)carbonyl, optionally substituted by fluorine, chlorine or hydroxyl, $C_1$–$C_4$-alkoxy, oxo, phenyl;
($C_5$–$C_6$-cycloalkenyl)-($C_1$–$C_3$-alkyl)carbonyl, optionally substituted by fluorine, chlorine or hydroxyl, $C_1$–$C_4$-alkoxy, oxo, phenyl;
$C_1$–$C_8$-alkyloxycarbonyl, optionally substituted by fluorine, chlorine, bromine, hydroxyl, $C_1$–$C_4$-alkoxy, $C_1$–$C_4$-alkylamino, di($C_1$–$C_4$-alkyl)amino, $C_1$–$C_4$-alkylthio;
$C_2$–$C_8$-alkenyloxycarbonyl, optionally substituted by fluorine, chlorine, hydroxyl, $C_1$–$C_4$-alkoxy, oxo, phenyl;
$C_2$–$C_8$-alkenyloxycarbonyl, optionally substituted by fluorine, chlorine, hydroxyl, $C_1$–$C_4$-alkoxy, oxo, phenyl;
$C_1$–$C_6$-alkylthiocarbonyl, optionally substituted by fluorine, chlorine, hydroxyl, $C_1$–$C_4$-alkoxy, oxo, phenyl;
$C_2$–$C_8$-alkenylthiocarbonyl, optionally substituted by fluorine, chlorine, hydroxyl, $C_1$–$C_4$-alkoxy, oxo, phenyl;
$C_1$–$C_8$-alkylamino- and di($C_1$–$C_8$-alkyl) aminocarbonyl, in each case optionally substituted by fluorine, chlorine, hydroxyl, $C_1$–$C_4$-alkoxy, oxo, phenyl;
pyrrolidin-1-yl, morpholino, piperidino-, piperazinyl-, or 4-methylpiperazin-1-ylcarbonyl, in each case optionally substituted by $C_1$–$C_4$-alkyl, $C_2$–$C_6$-alkenyl, $C_1$–$C_4$-acyl, oxo, thioxo, carboxyl, or phenyl;
$C_2$–$C_8$-alkenylamino- and di($C_1$–$C_6$-alkenyl) aminocarbonyl, in each case optionally substituted by fluorine, chlorine, hydroxyl, $C_1$–$C_4$-alkoxy, oxo, phenyl;
$C_1$–$C_6$-alkylsulfonyl, optionally substituted by fluorine, chlorine, hydroxyl, $C_1$–$C_4$-alkoxy, oxo, phenyl;
$C_1$–$C_6$-alkenylsulfonyl, optionally substituted by fluorine, chlorine, hydroxyl, $C_1$–$C_4$-alkoxy, oxo, phenyl;
or aryl, arylcarbonyl, aryl(thiocarbonyl), (arylthio)carbonyl, (arylthio)thiocarbonyl, aryloxycarbonyl, arylaminocarbonyl, (arylamino)thiocarbonyl, arylalkylaminocarbonyl, arylsulfonyl, arylalkyl, arylalkenyl, arylalkynyl, arylalkylcarbonyl, arylalkenylcarbonyl, arylalkoxycarbonyl or aryl(alkylthio)carbonyl, each of which is substituted by up to five radicals $R^6$ which are independent of one another, it being possible for the alkyl radical to contain in each case 1 to 5 carbon atoms, and $R^6$ being as defined above,
or heteroaryl, heteroarylalkyl, heteroarylalkenyl, heteroarylalkylcarbonyl or heteroarylalkenylcarbonyl, heteroaryloxycarbonyl, (heteroarylthio)carbonyl, heteroarylaminocarbonyl, heteroarylalkyloxycarbonyl, heteroaryl(alkylthio)carbonyl or heteroarylalkylaminocarbonyl, each of which is substituted by up to three radicals $R^6$ which are independent of one another, it being possible for the alkyl radical to contain in each case 1 to 3 carbon atoms,
$R^3$ and $R^4$ are identical or different and, independently of one another, are hydrogen, $C_1$–$C_8$-alkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;
$C_2$–$C_8$-alkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;
$C_3$–$C_8$-cycloalkyl, optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;
$C_3$–$C_8$-cycloalkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;
aryl, arylalkyl, heteroaryl or heteroarylalkyl, each of which is substituted by up to five radicals $R^6$ which are independent of one another, it being possible for the alkyl radical to contain 1 to 3 carbon atoms in each case, and $R^6$ being as defined above, $R^3$ and $R^4$ can furthermore also be
part of a saturated or unsaturated carbo- or heterocyclic ring which has 3 to 8 carbon atoms and which can optionally be substituted by fluorine, chlorine, hydroxyl, amino, $C_1$–$C_6$-alkyl, $C_2$–$C_6$-alkenyl, $C_2$–$C_6$-alkynyl, $C_1$–$C_6$-acyloxy, benzoyloxy, $C_1$–$C_6$-alkoxy, oxo, thioxo, carboxyl, carbamoyl or phenyl, X is oxygen, sulfur, selenium or substituted nitrogen N—$R^2$, it being possible for $R^2$ to have the abovementioned meanings, with the exception of those compounds in which $R^3$ and $R^4$ are both hydrogen, and compounds in which $R^2$ and $R^5$ are hydrogen and $R^3$ and/or $R^4$ are/is arylalkyl, and compounds in which X is oxygen and $R^2$ and $R^5$ are hydrogen.

In a preferred group of compounds of the formula I or Ia,
2) n is
  zero,
  one,
  two
  or three,
the individual substituents $R^1$ independently of one another are fluorine, chlorine, bromine, trifluoromethyl, trifluoromethoxy, hydroxyl, $C_1$–$C_4$-alkyl, $C_5$–$C_6$-cycloalkyl, $C_1$–$C_4$-alkoxy, ($C_1$–$C_4$-alkoxy)-($C_1$–$C_4$-alkoxy), $C_1$–$C_4$-alkylthio, $C_1$–$C_4$-alkylsulfinyl, $C_1$–$C_4$-alkylsulfonyl, nitro, amino, $C_1$–$C_4$-alkylamino, di($C_1$–$C_4$-alkyl)amino, piperidino, morpholino, 1-pyrrolidinyl, 4-methylpiperazinyl, thiomorpholino, imidazolyl, $C_1$–$C_4$-acyl, $C_1$–$C_4$-acyloxy, $C_1$–$C_4$-acylamino, cyano, carbamoyl, carboxyl, ($C_1$–$C_4$-alkyl)oxycarbonyl, hydroxysulfonyl or sulfamoyl or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, 2-pyridyl, 3-pyridyl or 4-pyridyl radical which is substituted by up to two radicals $R^6$ which are independent of one another,
where $R^6$ can be
  fluorine, chlorine, bromine, cyano, trifluoromethyl, nitro, amino, $C_1$–$C_4$-alkyl, $C_3$–$C_7$-cycloalkyl, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkylamino, di($C_1$–$C_4$-alkyl)amino, ($C_1$–$C_4$-alkyl)oxycarbonyl, phenyl or phenoxy, $R^2$ is hydrogen and $R^5$ is
hydrogen, hydroxyl, cyano, amino,
$C_1$–$C_6$-alkyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_2$–$C_8$-alkenyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_3$–$C_8$-allenyl,
$C_3$–$C_8$-alkynyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_3$–$C_8$-cycloalkyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_3$–$C_8$-cycloalkenyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
($C_3$–$C_8$-cycloalkyl)-($C_1$–$C_2$-alkyl)
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
($C_3$–$C_8$-cycloalkenyl)-($C_1$–$C_2$-alkyl),
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_1$–$C_6$-alkylcarbonyl,
optionally substituted by
  fluorine, chlorine, bromine, iodine, cyano, amino, mercapto, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;
$C_2$–$C_6$-alkenylcarbonyl, optionally substituted by fluorine, chlorine or hydroxyl, $C_1$–$C_4$-alkoxy, oxo, phenyl;
($C_3$–$C_6$-cycloalkyl)carbonyl, optionally substituted by fluorine, chlorine or hydroxyl, $C_1$–$C_4$-alkoxy, oxo, phenyl;
($C_5$–$C_6$-cycloalkenyl)carbonyl, optionally substituted by fluorine, chlorine or hydroxyl, $C_1$–$C_4$-alkoxy, oxo, phenyl;
($C_3$–$C_6$-cycloalkyl)-($C_1$–$C_2$-alkyl)carbonyl, optionally substituted by fluorine, chlorine or hydroxyl, $C_1$–$C_4$-alkoxy, oxo, phenyl;
($C_5$–$C_6$-cycloalkenyl)-($C_1$–$C_2$-alkyl)carbonyl, optionally substituted by fluorine, chlorine or hydroxyl, $C_1$–$C_4$-alkoxy, oxo, phenyl;
$C_1$–$C_6$-alkyloxycarbonyl, optionally substituted by fluorine, chlorine, bromine, hydroxyl, $C_1$–$C_4$-alkoxy, $C_1$–$C_4$-alkylamino, di($C_1$–$C_4$-alkyl)amino, $C_1$–$C_4$-alkylthio;
$C_2$–$C_6$-alkenyloxycarbonyl, optionally substituted by fluorine, chlorine, hydroxyl, $C_1$–$C_4$-alkoxy, oxo, phenyl;
$C_2$–$C_6$-alkenyloxycarbonyl, optionally substituted by fluorine, chlorine, hydroxyl, $C_1$–$C_4$-alkoxy, oxo, phenyl;
$C_1$–$C_6$-alkylthiocarbonyl, optionally substituted by fluorine, chlorine, hydroxyl, $C_1$–$C_4$-alkoxy, oxo, phenyl;
$C_2$–$C_6$-alkenylthiocarbonyl, optionally substituted by fluorine, chlorine, hydroxyl, $C_1$–$C_4$-alkoxy, oxo, phenyl;

$C_1$–$C_6$-alkylamino- and di($C_1$–$C_6$-alkyl) aminocarbonyl, in each case optionally substituted by fluorine, chlorine, hydroxyl, $C_1$–$C_4$-alkoxy, oxo, phenyl;

pyrrolidin-1-yl, morpholino-, piperidino-, piperazinyl-, or 4-methylpiperazin-1-ylcarbonyl;

$C_2$–$C_6$-alkenylamino- and di($C_1$–$C_6$-alkenyl) aminocarbonyl, in each case optionally substituted by fluorine, chlorine, hydroxyl, $C_1$–$C_4$-alkoxy, oxo, phenyl;

$C_1$–$C_4$-alkylsulfonyl, optionally substituted by fluorine, chlorine, hydroxyl, $C_1$–$C_4$-alkoxy, oxo, phenyl;

$C_1$–$C_4$-alkenylsulfonyl, optionally substituted by fluorine, chlorine, hydroxyl, $C_1$–$C_4$-alkoxy, oxo, phenyl;

or aryl, arylcarbonyl, aryl(thiocarbonyl), (arylthio) carbonyl, (arylthio)thiocarbonyl, aryloxycarbonyl, arylaminocarbonyl, (arylamino)thiocarbonyl, arylalkylaminocarbonyl, arylsulfonyl, arylalkyl, arylalkenyl, arylalkynyl, arylalkylcarbonyl, arylalkenylcarbonyl, aryl(alkylthio)carbonyl or arylalkoxycarbonyl, each of which is substituted by up to three radicals $R^6$ which are independent of one another, it being possible for the alkyl radical to contain in each case 1 to 5 carbon atoms and $R^6$ being as defined above, or 1- or 2-naphthylmethyl, 2-, 3- or 4-picolyl, 2- or 3-furylmethyl, 2- or 3-thienylmethyl, 2- or 3-pyrrolylmethyl, 2-, 3- or 4-pyridylcarbonyl, 2- or 3-furylcarbonyl, 2- or 3-thienylcarbonyl, 2- or 3-thienylacetyl, 2-, 3- or 4-picolyloxycarbonyl, 2- or 3-furylmethyloxycarbonyl, 2- or 3-thienylmethyloxycarbonyl, each of which is substituted by up to two radicals $R^6$ which are independent of one another, and $R^3$ and $R^4$ are identical or different and independently of one another are hydrogen, $C_1$–$C_6$-alkyl, optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_8$-alkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl; $C_3$–$C_8$-cycloalkyl, optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsufonyl, $C_1$–$C_4$-alkylsulfinyl, carboxyl or carbamoyl;

$C_3$–$C_8$-cycloalkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

aryl, arylalkyl, heteroaryl or heteroarylalkyl, each of which is substituted by up to three radicals $R^6$ which are independent of one another, it being possible for the alkyl radical to contain in each case 1 to 3 carbon atoms and $R^6$ being as defined above, $R^3$ and $R^4$ can furthermore also be part of a saturated or unsaturated carbo- or heterocyclic ring which has 3 to 7 carbon atoms and which can optionally be substituted by fluorine, chlorine, hydroxyl, amino, $C_1$–$C_4$-alkyl, $C_2$–$C_4$-alkenyl, $C_2$–$C_4$-alkynyl, $C_1$–$C_4$-acyloxy, benzoyloxy, $C_1$–$C_4$-alkoxy, oxo, thioxo, carboxyl, carbamoyl or phenyl, and X is oxygen, sulfur or selenium.

In a yet more preferred group of compounds of the formula I or Ia, 3) n is zero, one or two, the individual substituents $R^1$ independently of one another are fluorine, chlorine, bromine, trifluoromethyl, hydroxyl, $C_1$–$C_4$-alkyl, $C_1$–$C_4$-alkoxy, ($C_1$–$C_4$-alkoxy)- ($C_1$–$C_4$-alkoxy), $C_1$–$C_4$-alkylthio, nitro, amino, $C_1$–$C_4$-alkylamino, di($C_1$–$C_4$-alkyl)amino, piperidino, morpholino, 1-pyrrolidinyl, 4-methylpiperazinyl, $C_1$–$C_4$-acyl, $C_1$–$C_4$-acyloxy, $C_1$–$C_4$-acylamino, cyano, carbamoyl, carboxyl, ($C_1$–$C_4$-alkyl)oxycarbonyl, hydroxysulfonyl or sulfamoyl, or a phenyl, phenoxy, phenylthio, phenylsulfonyl, phenoxysulfonyl, benzoyl, 2-pyridyl, 3-pyridyl or 4-pyridyl radical which is substituted by up to two radicals $R^6$ which are independent of one another, where $R^6$ can be fluorine, chlorine, bromine, cyano, trifluoromethyl, nitro, amino, $C_1$–$C_4$-alkyl, $C_1$–$C_4$-alkoxy, ($C_1$–$C_4$-alkyl)oxycarbonyl, phenyl or phenoxy, $R^2$ is hydrogen and $R^5$ is $C_1$–$C_6$-alkyl, optionally substituted by fluorine, chlorine, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;

$C_2$–$C_6$-alkenyl, optionally substituted by fluorine, chlorine, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;

$C_3$–$C_8$-allenyl, $C_3$–$C_8$-alkynyl, optionally substituted by fluorine, chlorine, hydroxyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, oxo, thioxo, carboxyl or carbamoyl;

$C_3$–$C_8$-cycloalkyl, optionally substituted by fluorine, chlorine, hydroxyl, $C_1$–$C_4$-alkyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, oxo, thioxo, carboxyl or carbamoyl;

$C_3$–$C_8$-cycloalkenyl,
optionally substituted by
fluorine, chlorine, hydroxyl, $C_1$–$C_4$-alkyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, oxo, thioxo, carboxyl or carbamoyl;

($C_3$–$C_6$-cycloalkyl)-($C_1$–$C_2$-alkyl),
optionally substituted by
fluorine, chlorine, hydroxyl, $C_1$–$C_4$-alkyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, oxo, thioxo, carboxyl or carbamoyl;

($C_3$–$C_6$-cycloalkenyl)-($C_1$–$C_2$-alkyl),
optionally substituted by
fluorine, chlorine, hydroxyl, $C_1$–$C_4$-alkyl, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl) amino, $C_1$–$C_4$-alkylthio, oxo, thioxo, carboxyl or carbamoyl;

$C_1$–$C_6$-alkylcarbonyl,
optionally substituted by
fluorine, chlorine, hydroxyl, $C_1$–$C_4$-alkyl, $C_1$–$C_4$-acyloxy, benzoyloxy, benzyloxy, phenoxy, $C_1$–$C_4$-alkoxy, $C_1$–$C_4$-alkylamino, $C_1$–$C_4$-alkenylamino, di($C_1$–$C_4$-alkyl)amino, 1-pyrrolidinyl, piperidino, morpholino, 4-methylpiperazin-1-yl, $C_1$–$C_4$-alkylthio, oxo, thioxo, carboxyl or carbamoyl;

$C_2$–$C_6$-alkenylcarbonyl, optionally substituted by fluorine, chlorine or hydroxyl;
($C_3$–$C_6$-cycloalkyl)carbonyl,
($C_5$–$C_6$-cycloalkenyl)carbonyl,
($C_3$–$C_6$-cycloalkyl)-($C_1$–$C_2$-alkyl)carbonyl,
($C_5$–$C_6$-cycloalkenyl)-($C_1$–$C_2$-alkyl)carbonyl,
$C_1$–$C_6$-alkyloxycarbonyl, optionally substituted by fluorine, chlorine, bromine, hydroxyl, $C_1$–$C_4$-alkoxy, $C_1$–$C_4$-alkylamino, di($C_1$–$C_4$-alkyl)amino or $C_1$–$C_4$-alkylthio;
$C_2$–$C_6$-alkenyloxycarbonyl, optionally substituted by fluorine, chlorine, hydroxyl, $C_1$–$C_4$-alkoxy;
$C_2$–$C_6$-alkenyloxycarbonyl, optionally substituted by fluorine, chlorine, hydroxyl, $C_1$–$C_4$-alkoxy;
$C_1$–$C_6$-alkylthiocarbonyl, optionally substituted by fluorine, chlorine, hydroxyl, $C_1$–$C_4$-alkoxy;
$C_2$–$C_6$-alkenylthiocarbonyl, optionally substituted by fluorine, chlorine, hydroxyl, $C_1$–$C_4$-alkoxy;
$C_1$–$C_6$-alkylamino- and di($C_1$–$C_6$-alkyl) aminocarbonyl, in each case optionally substituted by fluorine, chlorine, hydroxyl, $C_1$–$C_4$-alkoxy;
pyrrolidin-1-yl, morpholino-, piperidino-, piperazinyl-, or 4-methylpiperazin-1-ylcarbonyl;
$C_2$–$C_6$-alkenylamino- and di($C_1$–$C_6$-alkenyl) aminocarbonyl, in each case optionally substituted by fluorine, chlorine, hydroxyl, $C_1$–$C_4$-alkoxy;
$C_1$–$C_4$-alkylsulfonyl, optionally substituted by fluorine, chlorine, hydroxyl, $C_1$–$C_4$-alkoxy;
$C_1$–$C_4$-alkenylsulfonyl;
or aryl, arylcarbonyl, (arylthio)carbonyl, aryloxycarbonyl, arylaminocarbonyl, (arylamino) thiocarbonyl, arylsulfonyl, arylalkylaminocarbonyl, arylalkyl, arylalkenyl, arylalkylcarbonyl, arylalkoxycarbonyl or aryl(alkylthio)carbonyl, each of which is substituted by up to two radicals $R^6$ which are independent of one another, it being possible for the alkyl radical to contain in each case 1 to 3 carbon atoms, and $R^6$ being as defined above, or 1- or 2-naphthylmethyl, 2-, 3- or 4-picolyl, 2- or 3-furylmethyl, 2- or 3-thienylmethyl, 2- or 3-pyrrolylmethyl,
2-, 3- or 4-pyridylcarbonyl, 2- or 3-furylcarbonyl, 2- or 3-thienylcarbonyl, 2- or 3-thienylacetyl, 2-, 3- or 4-picolyloxycarbonyl, 2- or 3-furylmethyloxycarbonyl or 2- or 3-thienylmethyloxycarbonyl, each of which is substituted by up to two radicals $R^6$ which are independent of one another, and $R^3$ and $R^4$ are identical or different and independently of one another are hydrogen, $C_1$–$C_4$-alkyl, optionally substituted by fluorine, chlorine, hydroxyl, amino, mercapto, $C_1$–$C_4$-acyloxy, benzoyloxy, phenoxy, $C_1$–$C_4$-alkoxy, $C_1$–$C_4$-alkylamino, di($C_1$–$C_4$-alkyl) amino, $C_1$–$C_4$-alkylthio, $C_1$–$C_4$-alkylsulfonyl, $C_1$–$C_4$-alkylsulfinyl, carboxyl or carbamoyl;

$C_2$–$C_6$-alkenyl, optionally substituted by fluorine or chlorine;

$C_3$–$C_6$-cycloalkyl, optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkenyl, optionally substituted by fluorine or chlorine;

aryl, benzyl, heteroaryl or heteroarylmethyl, each of which is substituted by up to two radicals $R^6$ which are independent of one another, $R^3$ and $R^4$ can furthermore also be
part of a saturated or unsaturated carbo- or heterocyclic ring which has 3 to 6 carbon atoms and which can optionally be substituted by fluorine, chlorine, hydroxyl, amino, $C_1$–$C_4$-acyloxy, benzoyloxy, $C_1$–$C_4$-alkoxy, oxo, thioxo, carboxyl or carbamoyl, and X is oxygen or sulfur.

In a yet again preferred group of compounds of the formula I or Ia, 4) n is
zero,
one
or two, the individual substituents $R^1$ independently of one another are
fluorine, chlorine, bromine, trifluoromethyl, hydroxyl, $C_1$–$C_4$-alkyl, $C_1$–$C_4$-alkoxy, ($C_1$–$C_4$-alkoxy)-($C_1$–$C_2$-alkoxy), $C_1$–$C_4$-alkylthio, nitro, amino, $C_1$–$C_4$-alkylamino, di($C_1$–$C_4$-alkyl)amino, piperidino, morpholino, 1-pyrrolidinyl, 4-methylpiperazinyl, $C_1$–$C_4$-acyl, $C_1$–$C_4$-acyloxy, $C_1$–$C_4$-acylamino, cyano, carbamoyl, carboxyl, ($C_1$–$C_4$-alkyl)oxycarbonyl, hydroxysulfonyl or sulfamoyl or
a phenyl, phenoxy, phenylthio, phenylsulfonyl, phenoxysulfonyl, benzoyl, 2-pyridyl, 3-pyridyl or 4-pyridyl radical, each of which is substituted by up to two radicals $R^6$ which are independent of one another, where $R^6$ can be
fluorine, chlorine, bromine, cyano, trifluoromethyl, nitro, amino, $C_1$–$C_4$-alkyl, $C_1$–$C_4$-alkoxy, ($C_1$–$C_4$-alkyl)oxycarbonyl, phenyl or phenoxy, $R^2$ is hydrogen and $R^5$ is
$C_1$–$C_6$-alkyl, optionally substituted by $C_1$–$C_4$-alkoxy or $C_1$–$C_4$-alkylthio;

$C_2$–$C_6$-alkenyl,
optionally substituted by oxo;

$C_3$–$C_6$-allenyl;

$C_3$–$C_8$-alkynyl, in particular 2-butynyl;

$C_3$–$C_6$-cycloalkyl;

$C_5$–$C_6$-cycloalkenyl;

($C_3$–$C_6$-cycloalkyl)-($C_1$–$C_2$-alkyl), in particular cyclopropylmethyl, optionally substituted by $C_1$–$C_4$-alkyl;

($C_3$–$C_6$-cycloalkenyl)-($C_1$–$C_2$-alkyl), in particular cyclohexenylmethyl;

$C_1$–$C_6$-alkylcarbonyl,
optionally substituted by
fluorine, chlorine, hydroxyl, benzyloxy, phenoxy, $C_1$–$C_4$-alkoxy, $C_1$–$C_4$-alkylamino, $C_1$–$C_4$-alkenylamino, di($C_1$–$C_4$-alkyl)amino, 1-pyrrolidinyl, piperidino, morpholino, 4-methylpiperazin-1-yl or $C_1$–$C_4$-alkylthio;

$C_2$–$C_6$-alkenylcarbonyl;

$C_1$–$C_6$-alkyloxycarbonyl, optionally substituted by fluorine, chlorine, bromine, hydroxyl, $C_1$–$C_4$-alkoxy, $C_1$–$C_4$-alkylamino, di($C_1$–$C_4$-alkyl)amino or $C_1$–$C_4$-alkylthio;

$C_2$–$C_6$-alkenyloxycarbonyl, in particular vinyloxycarbonyl, allyloxycarbonyl, isopropenyloxycarbonyl, butenyloxycarbonyl or pentenyloxycarbonyl;

$C_2$–$C_6$-alkynyloxycarbonyl, in particular propynyloxycarbonyl or butynyloxycarbonyl;

$C_1$–$C_6$-alkylthiocarbonyl;

$C_2$–$C_6$-alkenylthiocarbonyl, in particular allylthiocarbonyl;

$C_1$–$C_6$-alkylamino- and di($C_1$–$C_6$-alkyl)aminocarbonyl;

pyrrolidin-1-yl, morpholino-, piperidino-, piperazinyl-, or 4-methylpiperazin-1-ylcarbonyl;

$C_2$–$C_6$-alkenylamino- and di($C_1$–$C_6$-alkenyl)aminocarbonyl;

$C_1$–$C_4$-alkylsulfonyl;

$C_1$–$C_4$-alkenylsulfonyl;

or aryl which is substituted by up to two radicals $R^6$ which are independent of one another, in particular phenyl, arylcarbonyl, in particular benzoyl, (arylthio)carbonyl, aryloxycarbonyl, arylaminocarbonyl, (arylamino)thiocarbonyl, arylalkylaminocarbonyl, arylsulfonyl, arylalkyl, in particular benzyl, phenylethyl, arylalkenyl, arylalkylcarbonyl, arylalkoxycarbonyl or aryl (alkylthio)carbonyl, it being possible for the alkyl radical to contain in each case 1 to 3 carbon atoms and $R^6$ being as defined above, or 1- or 2-naphthylmethyl, 2-, 3- or 4-picolyl, 2- or 3-furylmethyl, 2- or 3-thienylmethyl, 2- or 3-pyrrolylmethyl, 2-, 3- or 4-pyridylcarbonyl, 2- or 3-furylcarbonyl, 2- or 3-thienylcarbonyl, 2- or 3-thienylacetyl, 2-, 3- or 4-picolyloxycarbonyl, 2- or 3-furylmethyloxycarbonyl, or 2- or 3-thienylmethyloxycarbonyl, each of which is substituted by up to two radicals $R^6$ which are independent of one another, and $R^3$ and $R^4$ are identical or different and independently of one another are
hydrogen,
$C_1$–$C_4$-alkyl,
optionally substituted by hydroxyl, mercapto, $C_1$–$C_4$-alkoxy, $C_1$–$C_4$-alkylthio, $C_1$–$C_4$-alkylsulfonyl, $C_1$–$C_4$-alkylsulfinyl, carboxyl or carbamoyl;

$C_2$–$C_6$-alkenyl,
aryl, benzyl, thienyl or thienylmethyl, each of which is substituted by up to two radicals $R^6$ which are independent of one another, $R^6$ being as defined above, $R^3$ and $R^4$ can also be
part of a saturated or unsaturated carbo- or heterocyclic ring which has 3 to 6 carbon atoms and can optionally be substituted by oxo or thioxo, and X is oxygen or sulfur.

Compounds of the formula I or Ia as defined above wherein the substituents mentioned have the following meanings are very particularly important:

n is
zero or
one, the individual substituents $R^1$ independently of one another are fluorine, chlorine, bromine, $C_1$–$C_2$-alkyl, $C_1$–$C_2$-alkoxy, $C_2$–$C_4$-acyl or cyano, $R^2$ is hydrogen and $R^5$ is
$C_2$–$C_6$-alkenyl,
$C_3$–$C_8$-alkynyl, in particular 2-butynyl;
($C_3$–$C_6$-cycloalkyl)-($C_1$–$C_2$-alkyl), in particular cyclopropylmethyl, optionally substituted by $C_1$–$C_4$-alkyl;
($C_3$–$C_6$-cycloalkenyl)-($C_1$–$C_2$-alkyl), in particular cyclohexenylmethyl;
$C_2$–$C_6$-alkylcarbonyl,
$C_2$–$C_6$-alkenylcarbonyl;
$C_1$–$C_6$-alkyloxycarbonyl;
$C_2$–$C_6$-alkenyloxycarbonyl, in particular vinyloxycarbonyl, allyloxycarbonyl, isopropenyloxycarbonyl, butenyloxycarbonyl or pentenyloxycarbonyl;
$C_2$–$C_6$-alkynyloxycarbonyl, in particular propynyloxycarbonyl or butynyloxycarbonyl;
$C_2$–$C_6$-alkenylthiocarbonyl, in particular allylthiocarbonyl;
$C_1$–$C_4$-alkylsulfonyl;
$C_1$–$C_4$-alkenylsulfonyl;

or arylalkyl, in particular benzyl or arylalkenyl, which is substituted by up to two radicals $R^6$ which are independent of one another, it being possible for the alkyl radical to contain in each case 1 to 3 carbon atoms and for the alkenyl radical to contain 2–3 carbon atoms, or 1-naphthylmethyl, 2- or 3-picolyl, 2-furylmethyl or 2- or 3-thienylmethyl, each of which is substituted by up to two radicals $R^6$ which are independent of one another, where $R^6$ is
fluorine, chlorine, bromine, cyano, $C_1$–$C_2$-alkyl or $C_1$–$C_2$-alkoxy, and $R^3$ and $R^4$ are identical or different and independently of one another are
hydrogen,
$C_1$–$C_4$-alkyl,
optionally substituted by hydroxyl, mercapto, $C_1$–$C_4$-alkoxy, $C_1$–$C_2$-alkylthio, and X is oxygen or sulfur.

The alkyl groups in the above definitions can be straight-chain or branched. Unless otherwise defined, they preferably contain 1–8, particularly preferably 1–6, in particular 1–4, carbon atoms. Examples are the methyl, ethyl, propyl, 1-methylethyl, butyl, 1-methylpropyl, 2-methylpropyl and 1,1-dimethylethyl group, and similar groups.

The alkenyl groups mentioned in the above definitions can be straight-chain or branched and contain 1 to 3 double bonds. Unless otherwise defined, these groups preferably contain 2–8, in particular 2–6, carbon atoms. Examples are the 2-propenyl, 1-methylethenyl, 2-butenyl, 3-butenyl, 2-methyl-2-propenyl, 3-methyl-2-butenyl, 2,3-dimethyl-2-butenyl, 3,3-dichloro-2-propenyl and pentadienyl groups and similar groups.

The alkynyl groups mentioned in the above definitions can be straight-chain or branched and contain 1 to 3 triple bonds. Unless otherwise defined, they contain preferably 2–8, particularly preferably 3–6, carbon atoms. Examples are the 2-propynyl and 3-butynyl group and similar groups.

Unless otherwise defined, the cycloalkyl and cycloalkenyl groups mentioned in the above definitions contain preferably 3–8, particularly preferably 4–6, carbon atoms. Examples are the cyclopropyl, cyclobutyl, cyclopentyl, cyclopentenyl, cyclohexyl or cyclohexenyl group.

The acyl groups mentioned in the above definitions can be aliphatic, cycloaliphatic or aromatic. Unless otherwise defined, they preferably contain 1–8, particularly preferably 2–7, carbon atoms. Examples of acyl groups are the formyl, acetyl, chloroacetyl, trifluoroacetyl, hydroxyacetyl, propionyl, butyryl, isobutyryl, pivaloyl, cyclohexanoyl or benzoyl group.

The aryl groups mentioned in the above definitions are preferably aromatic groups having 6–14 carbon atoms, in particular 6–10 carbon atoms, for example phenyl or naphthyl.

Suitable hetero atoms in the abovementioned heterocyclic rings or heteroaryl groups are, in particular, oxygen, sulfur and nitrogen, where, in the case of a nitrogen-containing ring which is saturated in this position, a structure N—Z is present in which Z is H or $R^5$ with the individual above-described definitions.

Unless otherwise defined, the heterocyclic rings preferably have 1–13 carbon atoms and 1–6 hetero atoms, in particular 3–9 carbon atoms and 1–4 hetero atoms.

Suitable radicals for the heteroaryl groups mentioned in the above definitions are, for example, heteroaromatic radicals such as 2- or 3-thienyl, 2- or 3-furyl, 2-, 3- or 4-pyridyl, pyrimidyl, indolyl, quinolyl or isoquinolyl.

Examples of the aralkyl groups mentioned in the above definitions are benzyl, phenylethyl, naphthylmethyl or styryl.

The abovementioned substituents $R^1$ to $R^5$ are preferably trisubstituted, particularly preferably disubstituted, in particular monosubstituted, by the particular substituents mentioned.

In the case of the particular definitions of composite substituents (such as, for example, arylalkoxycarbonyl), the ranges which have been described above as being preferred for the individual substituents are also preferred.

Depending on the various substituents, compounds of the formulae I and Ia can have several asymmetric carbon atoms. The invention therefore relates both to the pure stereoisomers and to mixtures thereof such as, for example, the corresponding racemate.

The pure stereoisomers of the compounds of the formulae I and Ia can be prepared directly by known methods or analogously to known methods, or they can be resolved later.

The compounds of the formulae I and Ia can be prepared by known methods or modifications thereof (see, for example, Rodd's Chemistry of Carbon Compounds, S. Coffey, M. F. Ansell (Editor); Elsevier, Amsterdam, 1989; Vol. IV Part IJ, p. 301–311. Heterocyclic Compounds. R. C. Elderfield (Editor); Wiley, New York, 1957; Vol. 6, p. 491–495).

The present invention furthermore includes a process for the preparation of compounds of the formulae I and Ia as explained in 1)–4) above, which comprises A) for preparing compounds of the formula I where X is oxygen and the radicals $R^1$, $R^2$, $R^3$, $R^4$ and $R^5$ are as defined under 1)–4), reacting a compound of the formula II

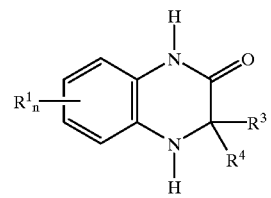

(II)

with the definitions mentioned under 1)–4) applying to $R^1$, $R^3$ and $R^4$, with a compound of the formula III

R—Z (III)

where R has the meanings for $R^5$ and $R^2$ which have been mentioned above under 1)–4) with the exception of hydrogen, hydroxyl, $C_1$–$C_6$-alkoxy, aryloxy, $C_1$–$C_6$-acyloxy, amino, $C_1$–$C_6$-alkylamino, di($C_1$–$C_6$-alkyl)amino, arylamino and $C_1$–$C_6$-acylamino, and Z is a leaving group, or B) preparing compounds of the formula I where X is sulfur and $R^1$, $R^2$, $R^3$, $R^4$ and $R^5$ are as defined under 1)–4) by reacting a compound of the formula I where X is oxygen and the definitions mentioned under 1)–4) apply to $R^1$, $R^2$, $R^3$, $R^4$ and $R^5$, with a sulfurizing reagent, or C) preparing compounds of the formula Ia where X and the radicals $R^1$ to $R^5$ are as defined under 1)–4), by reacting a compound of the formula IV

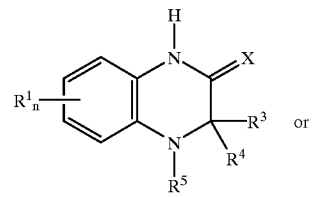

(IV)

or

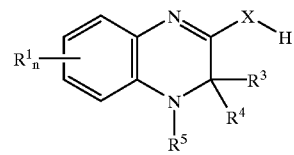

(IVa)

where the definitions mentioned under 1)–4) apply to $R^1$, $R^3$, $R^4$ and $R^5$, with a compound of the formula III $R^2$—Z (III)

where the definitions described under 1)–4) for formula I and Ia apply to $R^2$, with the exception of hydrogen, hydroxyl, $C_1$–$C_6$-alkoxy, aryloxy, $C_1$–$C_6$-acyloxy, amino, $C_1$–$C_6$-alkylamino, di($C_1$–$C_6$-alkyl)amino, arylamino or $C_1$–$C_6$-acylamino, and Z is a leaving group, or D) preparing compounds of the formula I where X is oxygen and the radicals $R^1$ to $R^5$ are as defined under 1)–4) by cyclizing a compound of the formula V

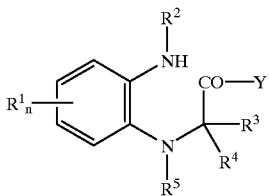

where $R^1$ to $R^5$ are as defined under 1)–4) and Y is hydroxyl, $C_1$–$C_4$-alkoxy, optionally halogenated $C_1$–$C_4$-acyloxy, chlorine, bromine or iodine, or E) preparing compounds of the formula I where X is oxygen, $R^4$ and $R^5$ are hydrogen and the definitions mentioned under 1)–4) apply to $R^1$ to $R^3$, from the quinoxalinones of the formula Xl

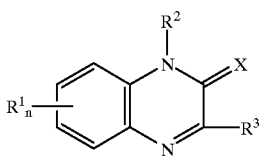

where $R^1$ to $R^3$ are as defined under 1)–4), by addition of hydrogen on the C=N bond, or F) preparing compounds of the formula I where X is oxygen and $R^1$ to $R^5$ are as defined under 1)–4), from compounds of the formula VI

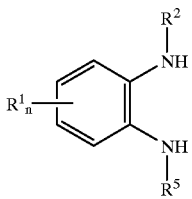

where $R^1$, $R^2$ and $R^5$ are as defined under 1)–4), by reacting them with chloroform or bromoform and a carbonyl compound of the formula XIII $$R^3\text{—CO—}R^4 \qquad (XIII)$$

where $R^3$ and $R^4$ are as defined under 1)–4), or with α-(trihalomethyl)alkanols of the formula XIV $$Hal^3C\text{—}C(OH)\text{—}R^3R^4 \qquad (XIV)$$

where Hal is Cl, Br or I,
in which $R^3$ and $R^4$ are as defined under 1)–4), or G) preparing compounds of the formula I where X is oxygen and $R^1$, $R^2$, $R^3$, $R^4$ and $R^5$ are as defined under 1)–4), by reacting a compound of the formula I where X is oxygen and the definitions mentioned under 1)–4) apply to $R^1$, $R^2$, $R^5$ and to $R^3$ and $R^4$, with the exception that at least one of the radicals $R^3$ or $R^4$ is hydrogen, with an alkylating reagent of the formula XV $$R'\text{—Z} \qquad (XV)$$

where R' has the meanings mentioned above for $R^3$ and $R^4$ with the exception of hydrogen and Z is a leaving group, or H) preparing compounds of the formula I where X is oxygen, $R^1$, $R^2$, $R^3$ and $R^4$ are as defined under 1)–4) and $R^5$ is $C_1$–$C_8$-alkyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl, carbamoyl, $C_3$–$C_8$-alkenyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl) amino, $C_1$–$C_6$-alkylthio, cyano, carboxyl or carbamoyl, $C_3$–$C_8$-alkynyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl or carbamoyl, $C_4$–$C_8$-cycloalkyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl or carbamoyl, $C_5$–$C_8$-cycloalkenyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, $C_1$–$C_6$-dialkylamino, $C_1$–$C_6$-alkylthio, cyano, carboxyl or carbamoyl, ($C_1$–$C_6$-alkoxy)-($C_1$–$C_6$-alkyl), di($C_1$–$C_6$-alkylamino)-($C_1$–$C_6$-alkyl) or ($C_3$–$C_6$-cycloalkyl)alkyl, ($C_6$–$C_8$-cycloalkenyl)alkyl, or arylalkyl, naphthylalkyl or heteroarylalkyl, each of which is substituted by up to five radicals $R^6$ which are independent of one another, it being possible for the alkyl radical to contain in each case 1 to 3 carbon atoms, by reductive alkylation of a compound of the formula I where $R^5$ is hydrogen and X is oxygen and the definitions mentioned under 1)–4) apply to $R^1$, $R^2$, $R^3$ and $R^4$, with a carbonyl compound of the formula XVI, $$R''\text{—C(=O)—}R''' \qquad (XVI)$$

where R" and R'" are identical or different and independently of one another are hydrogen, $C_1$–$C_7$-alkyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl or carbamoyl, $C_3$–$C_7$-alkenyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl or carbamoyl, $C_3$–$C_7$-alkynyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl) amino, $C_1$–$C_6$-alkylthio, cyano, carboxyl or carbamoyl, $C_4$–$C_8$-cycloalkyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$-alkyl)amino, $C_1$–$C_6$-alkylthio, cyano, carboxyl or carbamoyl, $C_6$-cycloalkenyl, optionally substituted by fluorine, chlorine, bromine, iodine, hydroxyl, $C_1$–$C_6$-acyloxy, benzoyloxy, phenoxy, $C_1$–$C_6$-alkoxy, $C_1$–$C_6$-alkylamino, di($C_1$–$C_6$- alkyl)amino, $C_1$–$C_6$-alkylthio, cyano, carboxyl or carbamoyl, ($C_1$–$C_6$-alkoxy)-($C_1$–$C_5$-alkyl), [di($C_1$–$C_6$-alkyl)amino]-($C_1$–$C_5$-alkyl) or ($C_4$–$C_6$-cycloalkyl) alkyl, ($C_6$-cycloalkenyl)alkyl, or arylalkyl, naphthylalkyl or heteroarylalkyl, each of which is substituted by up to five radicals $R^6$ which are independent of one another, it being possible for the alkyl radical to contain in each case 0 to 2 carbon atoms, and where R" and R'" can be linked to each other to form a 4- to 8-membered ring, or I) preparing compounds of the formula I where X is oxygen and $R^1$, $R^2$, $R^3$ and $R^4$ are as defined under 1)–4) and $R^5$ is $C_1$–$C_8$-alkyloxycarbonyl, $C_1$–$C_8$-alkylthiocarbonyl, $C_2$–$C_8$-alkenyloxycarbonyl, $C_2$–$C_8$-alkenylthiocarbonyl, $C_2$–$C_8$-alkynyloxycarbonyl, $C_1$–$C_6$-alkylaminocarbonyl, $C_3$–$C_6$-alkenylaminocarbonyl, di($C_1$–$C_6$-alkyl)aminocarbonyl, pyrrolidin-1-yl, morpholino-, piperidino-, piperazinyl-, 4-methylpiperazin-1-ylcarbonyl, optionally substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl; or aryloxycarbonyl, arylthio(carbonyl), arylaminocarbonyl, heteroaryloxycarbonyl, heteroarylthiocarbonyl, heteroarylaminocarbonyl, arylalkyloxycarbonyl, (arylalkylthio)carbonyl, arylalkylaminocarbonyl, heteroalkyloxycarbonyl, (heteroalkylthio)carbonyl or heteroalkylaminocarbonyl, each of which is substituted by up to five radicals $R^6$ which are independent of one another, it being possible for the alkyl radical to contain in each case 1 to 3 carbon atoms, by reacting a compound of the formula XVII

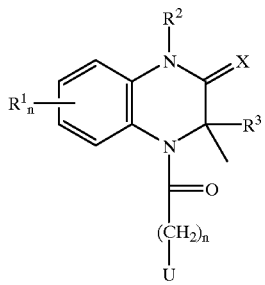

XVII where the definitions mentioned under 1)–4) apply to $R^1$, $R^2$, $R^3$ and $R^4$, n is 0, 1, 2 or 3, X is oxygen and U is a leaving group, with a compound of the formula XVIII Nu—H    (XVIII)

where Nu is $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_1$–$C_8$-alkylamino- and di($C_1$–$C_8$-alkyl)amino, $C_2$–$C_8$-alkenylamino- and di($C_1$–$C_6$-alkyl)amino, optionally substituted by fluorine, chlorine, bromine, hydroxyl, $C_1$–$C_4$-alkoxy, $C_1$–$C_4$-alkylamino, di($C_1$–$C_4$-alkyl)amino, $C_1$–$C_4$-alkylthio, pyrrolidin-1-yl, morpholino-, piperidino-, piperazinyl- or 4-methylpiperazin-1-ylcarbonyl, optionally substituted by $C_1$–$C_4$-alkyl, $C_2$–$C_6$-alkenyl, $C_1$–$C_4$-acyl, oxo, thioxo, carboxyl or phenyl, or aryloxy, arylthio, arylamino, arylalkyloxy, arylalkylthio, arylalkylamino, heteroaryloxy, heteroarylthio, heteroarylamino, heteroarylalkyloxy, heteroarylalkylthio or heteroarylalkylamino, each of which is substituted by up to five radicals $R^6$ ($R^6$ is as defined at the outset) which are independent of one another, it being possible for the alkyl radical to contain in each case 1 to 3 carbon atoms.

The abovementioned method A preferably proceeds under the following conditions:

The substituent Z in formula III is a suitable leaving group such as, for example, chlorine, bromine or iodine, a suitable radical of sulfuric acid, an aliphatic or aromatic sulfonate, or optionally halogenated acyloxy.

The reaction is expediently carried out in an inert solvent. Suitable solvents are, for example, aromatic hydrocarbons such as toluene or xylene, lower alcohols such as methanol, ethanol or 1-butanol, ethers such as tetrahydrofuran or glycol dimethyl ether, dipolar aprotic solvents such as N,N-dimethylformamide, N-methyl-2-pyrrolidone, acetonitrile, nitrobenzene, dimethyl sulfoxide, or mixtures of these solvents. Two-phase systems with aqueous solutions of bases in the presence of a phase transfer catalyst such as, for example, benzyltriethylammonium chloride, are also possible.

The presence of a suitable base, for example of an alkali metal carbonate, alkali metal hydrogen carbonate, alkaline earth metal carbonate or alkaline earth metal hydrogen carbonate such as sodium carbonate, calcium carbonate or sodium bicarbonate, of an alkali metal hydroxide or alkaline earth metal hydroxide such as potassium hydroxide or barium hydroxide, an alcoholate such as sodium ethanolate or potassium tert.-butylate, an organolithium compound such as butyllithium or lithiumdiisopropylamine, an alkali metal hydride or alkaline earth metal hydride such as sodium hydride or calcium hydride, an alkali metal fluoride such as potassium fluoride, or an organic base such as triethylamine or pyridine for scavenging the acid which is liberated during the reaction, may be expedient.

In some cases, the addition of an iodide, for example potassium iodide, is expedient. The reaction is generally carried out at temperatures between −10 and 160° C., preferably at room temperature.

To carry out this reaction, any nucleophilic substituents such as, for example, hydroxyl, mercapto or amino groups, with the exception of the 1- and/or 4-position in compounds of the formula II or III, must, before the reaction is carried out, be derivatized in a suitable manner or provided with conventional protective groups such as, for example, acetyl or benzyl, which can then be eliminated.

The sulfurizing reagent which is preferably used for the reaction as described above under B) is 2,4-bis(4-methoxyphenyl)-1,3-dithia-2,4-diphosphetane 2,4-disulfide (Lawesson's reagent), bis(tricyclohexyltin)sulfide, bis(tri-n-butyltin)sulfide, bis(triphenyltin)sulfide, bis(trimethylsilyl) sulfide or phosphorus pentasulfide. The reaction is carried out expediently in an organic solvent or in a solvent mixture, at room temperature or above, preferably at the boiling point of the reaction mixture, and, if possible, under anhydrous conditions. Suitable substances are, for example, carbon disulfide, toluene, xylene, pyridine and 1,2-dichloroethane. If the tin sulfides or silyl sulfides which have been mentioned are used, it is advisable to carry out the sulfurization reaction in the presence of a Lewis acid, such as boron trichloride.

In the presence of other carbonyl groups in a compound of the formula I, for example in a compound where X is oxygen and one or more radicals $R^1$ to $R^6$ are acyl, the carbonyl is to be protected by known methods prior to the sulfurization reaction by a suitable protective group, for example by acetalization; subsequent elimination of the protective groups results in the desired compound.

For the reaction described above under C, the substituent Z is a suitable leaving group, preferably chlorine, bromine or iodine, a suitable radical of sulfuric acid, an aliphatic or aromatic sulfonate, or optionally halogenated acyloxy.

The reaction conditions for this reaction correspond to those of method A.

The cyclization described under D) is effected in a suitable solvent such as methanol, ethanol, N,N-dimethylformamide or N-methylpyrrolidone, in the presence of a base; suitable bases are alkali metal carbonates, alkali metal hydrogen carbonates, alkaline earth metal carbonates or alkaline earth metal hydrogen carbonates such as sodium carbonate, calcium carbonate or sodium bicarbonate, alkali metal hydroxides or alkaline earth metal hydroxides such as potassium hydroxide or barium hydroxide, alcoholates such as sodium ethanolate or potassium tert.-butylate, organolithium compounds such as butyllithium or lithium diisopropylamine, alkali metal hydrides or alkaline earth metal hydrides such as sodium hydride or calcium hydride, or an organic base such as triethylamine or pyridine—the latter substances can also be used as solvents, or organic or mineral acids such as glacial acetic acid, trifluoroacetic acid, hydrochloric acid or phosphoric acid. The reaction is preferably carried out at temperatures between 20 and 120° C., particularly preferably at room temperature.

The compounds of the formula V, where $R^1$ to $R^5$ and Y are as defined under 1)–5), can be obtained from compounds of the formula VI

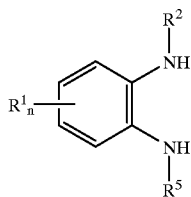

VI where $R^1$, $R^2$ and $R^5$ are as defined under 1)–4), by alkylation with a compound of the formula VII

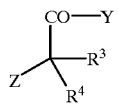

VII where $R^3$, $R^4$ and Y are as defined under 1)–5) and Z is as defined under A). The reaction conditions for this alkylation correspond to those given in method A.

Simultaneous cyclization to give the dihydroquinoxaline of the formula I takes place under suitable conditions.

Compounds of the formula V in which $R^1$, $R^3$ to $R^5$ and Y are as defined under 1)–5) and $R^2$ is hydrogen can also be prepared from compounds of the formula VIII

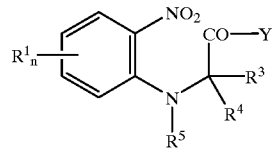

(VIII)

where $R^1$, $R^3$ to $R^5$ and Y are as defined under 1)–5) by reducing the nitro group by known processes to the amino group.

Simultaneous cyclization to give the dihydroquinoxaline of the formula I takes place under suitable conditions, for example by carrying out the reduction in the presence of an acid.

The reduction is carried out by standard methods (see, for example, Methoden der Organischen Chemie [Methods in Organic Chemistry] (Houben-Weyl), E. Müller (Editor); G. Thieme Verlag, Stuttgart, 1957; Vol. XI/1, p. 360–490), for example using tin(II) chloride in glacial acetic acid, $TiCl_3$ in hydrochloric acid, or by catalytic hydrogenation, the choice of reagent being determined by the chemical stability of the various substituents $R^1$ and $R^3$ to $R^5$; if, for example, one of the radicals is alkenyl, the first method will be selected to obtain the double bond.

The phenylenediamines of the formula VI which are required as starting materials for the syntheses described are known from the literature or commercially available or can be synthesized by methods known from the literature.

N-ortho-nitrophenylamino acid derivatives of the formula VIII, where $R^1_n$ and $R^3$ to $R^5$ are as defined under 1)–4) and Y is $OR^7$, where $R^7$ is hydrogen, $C_1$–$C_6$-alkyl, optionally in each case for example halogen-substituted phenyl, benzyl or 9-fluorenylmethyl, can be obtained for example by amination of ortho-halonitro aromatic substances of the formula IX

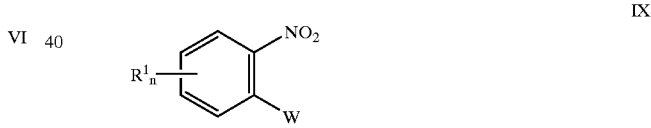

IX where $R^1$ is as defined under 1)–4) and W is fluorine, chlorine, bromine or iodine, with amino acids or their esters of the formula X

X where $R^3$, $R^4$, $R^5$ and $R^7$ are as defined under 1)–5). The reaction can be carried out in the presence of an inorganic or organic auxiliary base such as, for example, sodium carbonate, potassium carbonate, sodium hydroxide or triethylamine. It is advantageous to use an inert solvent at temperatures between 0 and 150° C., preferably at reflux temperature. Suitable solvents are open-chain or cyclic ethers, for example tetrahydrofuran or glycol dimethyl ether, aromatic hydrocarbons, for example toluene or chlorobenzene, alcohols, for example ethanol, isopropanol or glycol monomethyl ether, dipolar aprotic solvents, for example N,N-dimethylformamide, N-methyl-2-pyrrolidone or 1,3-dimethyl-tetrahydro-2(1H)-pyrimidinone.

The N-ortho-nitrophenylamino acids of the formula VIII where Y is hydroxyl can, if desired or necessary, be converted by well-known standard methods into the acid derivatives of the formula VIII where Y is hydroxyl, $C_1$–$C_4$-alkoxy, optionally halogenated $C_1$–$C_4$-acyloxy, chlorine, bromine or iodine.

Ortho-halonitroaromatic compounds of the formula IX and amino acids of the formula X are known from the literature and commercially available or can be prepared by methods known from the literature.

The reaction described above under E) is preferably effected by means of catalytic hydrogenation (using hydrogen) or hydrosilylation (using alkylsilanes, for example diphenylsilane) in the presence of a hydrogenation catalyst, for example Raney nickel or palladium-on-charcoal, at a hydrogen pressure of 1 to 5 bar, or by means of a reducing agent from the class of the complex metal hydrides such as sodium borohydride or sodium cyanoborohydride, or using metals, or metal salts, and acid such as, for example, zinc/glacial acetic acid or $SnCl_2$/HCl. It is advantageous to carry out the reaction in an inert solvent such as lower alcohols, for example methanol or isopropanol, ethers such as tetrahydrofuran or glycol dimethyl ether, dipolar aprotic solvents such as N,N-dimethylformamide, aromatic hydrocarbons such as toluene or xylene, or mixtures of these solvents, at temperatures between −20 and 100° C., preferably at room temperature.

If a chiral hydrogenation catalyst, for example di-$\mu$-chloro-bis[(cycloocta-1c,5c-diene)-rhodium(I)]/(+) or (−)4,5-bis-(diphenylphosphinomethyl)-2,2-dimethyl-1,3-dioxolane, or a chiral complex metal hydride, for example sodium tris-(N-benzyloxycarbonyl-L-prolinoyloxy)-borohydride, are used in the above-described reaction, the individual enantiomers can be prepared selectively.

If, in compounds of the formula XI, substituents are present which can be hydrogenated or reduced under the above-described conditions, for example oxo, it is necessary to use an intermediate of the formula XI with substituents which are not attacked, but which can be derivatized to give the group required, for example hydroxyl. The substituents can also be provided with a customary protective group, for example an acetal protective group, which can then be removed after the above-described reaction.

Quinoxalinones of the formula XI where $R^1$ to $R^3$ are as defined under 1)–4) can be obtained by known processes by condensing a phenylenediamine of the formula VI, where $R^1$ and $R^2$ are as defined under 1)–4) and $R^5$ is hydrogen, with an alpha-ketocarboxylic acid of the formula XII

$$R^3\text{—CO—COOH} \qquad\qquad\qquad (XII)$$

where $R^3$ is as defined under 1)–4).

The reaction is expediently carried out in an inert solvent in a temperature range of between 0 and 150° C.; examples of suitable solvents are alcohols, for example ethanol or isopropanol, open-chain or cyclic ethers, for example glycol dimethyl ether or tetrahydrofuran, or dipolar aprotic solvents, for example N,N-dimethylformamide or acetonitrile.

The reaction described above under F) is expediently carried out in a two-phase system composed of an organic solvent or solvent mixture which is not miscible with water, composed of, for example, halogenated hydrocarbons, for example dichloromethane or 1,2-dichloroethane, or aromatic hydrocarbons, for example toluene or xylene, and a concentrated aqueous solution of an alkali metal hydroxide or alkaline earth metal hydroxide, for example sodium hydroxide or barium hydroxide. The presence of a phase transfer catalyst such as, for example, benzyltriethylammonium chloride or tetrabutylammonium bromide, is advantageous.

The reaction is usually carried out at temperatures between 0 and 50° C., preferably at room temperature.

Substituents in compounds of the formulae VI and XIII, or XIV, which are not stable under the reaction conditions must be replaced by those which can be derivatized to the required group. The substituents can also be provided with a customary protective group which can then be removed after the above-described reaction.

In the reaction described above under G), Z in formula XV is a suitable leaving group such as, for example, chlorine, bromine or iodine, a suitable sulfuric acid radical, an aliphatic or aromatic sulfonate, or optionally halogenated acyloxy.

The reaction conditions for this reaction correspond to those in method A.

The reaction described under H) is preferably effected by catalytic hydrogenation (using hydrogen) in the presence of a hydrogenation catalyst, for example palladium-on-charcoal, at a hydrogen pressure of 1 to 5 bar, or by means of a reducing agent from the class of the complex metal hydrides, such as sodium borohydride, sodium triacetoxyborohydride or sodium cyanoborohydride.

The reaction is expediently carried out in an inert solvent, such as lower alcohols, for example methanol or isopropanol, ethers, for example tetrahydrofuran or glycol dimethyl ether, halogenated hydrocarbons, for example dichloromethane or dichloroethane, at temperatures between −20 and 100° C., preferably at room temperature. The presence of an acid such as, for example, acetic acid or trifluoroacetic acid, or of a Lewis acid such as, for example, titanium tetrachloride, is advantageous. If, in compounds of the formulae I and XVI, substituents are present which can be hydrogenated or reduced under the above-described conditions, for example oxo, the use of an intermediate of the formulae I and XVI with substituents which are not attacked but which can be derivatized to the required group, for example hydroxyl, is necessary. Acid-labile groups such as, for example, acetals, or groups which react under the reaction conditions, such as, for example, primary amines, are also to be avoided or to be provided with a customary protective group.

The reaction described under I) is expediently carried out in an inert solvent. Examples of suitable solvents are aromatic hydrocarbons such as toluene or xylene, lower alcohols such as methanol, ethanol or 1-butanol, ethers such as tetrahydrofuran or glycol dimethyl ether, dipolar aprotic solvents such as N,N-dimethylformamide, N-methyl-2-pyrrolidone, acetonitrile, nitrobenzene, dimethyl sulfoxide, or mixtures of these solvents. Two-phase systems with aqueous solutions of bases in the presence of a phase transfer catalyst such as, for example, benzyltriethylammonium chloride, are also possible.

The presence of a suitable base, for example an alkali metal hydroxide or alkaline earth metal hydroxide such as potassium hydroxide or barium hydroxide, of an alcoholate such as sodium ethanolate or potassium tert.-butylate, an organolithium compound such as butyllithium or lithium diisopropylamide, an alkali metal hydride or alkaline earth metal hydride such as sodium hydride or calcium hydride, an alkali metal fluoride such as potassium fluoride, or an organic base such as triethylamine or pyridine, may be useful. The reaction is usually carried out at temperatures between −10 and 160° C., preferably at room temperature.

To carry out this reaction, any nucleophilic substituents in compounds XVII and XVIII which do not participate in the reaction, such as, for example, hydroxyl, mercapto or amino groups, are to be derivatized in a suitable manner or to be provided with customary protective groups such as, for example, acetyl or benzyl, which can then be eliminated.

The compounds XVII which are required for the abovementioned reaction and in which the definitions described under 1)–4) apply to $R^1$, $R^2$, $R^3$ and $R^4$, n is 0, 1, 2 or 3, X is oxygen and U is a suitable leaving group, halogen such as, for example, chlorine, bromine, iodine, a halogenated aliphatic or aromatic alcoholate such as, for example, 2,2,2-trichloroethoxy, chlorophenoxy, or a heterocycle which is linked via nitrogen such as, for example, imidazolyl, triazolyl or benzotriazolyl, are prepared by reacting a compound of the formula I where $R^5$ is hydrogen and X is oxygen, and the definitions described under 1)–4) apply to $R^1$, $R^2$, $R^3$ and $R^4$, with a suitable carbonic acid derivative, for example phosgene, diphosgene, triphosgene, trichloroethyl chloroformate or carbonyldiimidazole, or with a suitable halo carbonyl halide, for example bromoacetyl chloride.

The reaction is expediently carried out in an inert solvent. Examples of suitable solvents are aromatic hydrocarbons such as toluene or xylene, ethers such as tetrahydrofuran or glycol dimethyl ether, or halogenated hydrocarbons such as dichloromethane or dichloroethane.

The presence of a suitable base, for example of an alkali metal hydroxide or alkaline earth metal hydroxide, such as potassium hydroxide or barium hydroxide, or an organic base such as triethylamine or pyridine, may be useful.

The reaction is usually carried out at temperatures between –30 and 160° C., preferably at room temperature.

The present invention furthermore relates to the compounds as described under 1) to 4) as pharmaceuticals, preferably for treating viral diseases, in particular diseases caused by HIV.

The invention furthermore relates to pharmaceuticals comprising at least one compound according to the invention, and to the use of the abovementioned compounds for the preparation of pharmaceuticals, preferably for the treatment of viral diseases, in particular for the treatment of diseases caused by HIV.

The present invention furthermore relates to the use of compounds of the abovementioned formula I or IA in which n is
  zero,
  one,
  two,
  three
  or four,
the individual substituents $R^1$ independently of one another are fluorine, chlorine, bromine, iodine, trifluoromethyl, trifluoromethoxy, hydroxyl, $C_1$–$C_8$-alkyl, $C_5$–$C_8$-cycloalkyl, $C_1$–$C_6$-alkoxy, ($C_1$–$C_6$-alkoxy)-($C_1$–$C_4$-alkoxy), $C_1$–$C_6$-alkylthio, $C_1$–$C_6$-alkylsulfinyl, $C_1$–$C_6$-alkylsulfonyl, nitro, amino, azido, $C_1$–$C_6$-alkylamino, di($C_1$–$C_6$-alkyl)amino, piperidino, morpholino, 1-pyrrolidinyl, 4-methylpiperazinyl, thiomorpholino, imidazolyl, triazolyl, tetrazolyl, $C_1$–$C_6$-acyl, $C_1$–$C_6$-acyloxy, $C_1$–$C_6$-acylamino, cyano, carbamoyl, carboxyl, ($C_1$–$C_6$-alkyl)oxycarbonyl, hydroxysulfonyl, sulfamoyl or
  a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, 2-pyridyl, 3-pyridyl or 4-pyridyl radical which is substituted by up to five radicals $R^6$ which are independent of one another, where $R^6$ can be
  fluorine, chlorine, bromine, iodine, cyano, trifluoromethyl, trifluoromethoxy, nitro, amino, azido, $C_1$–$C_6$-alkyl, $C_3$–$C_8$-cycloalkyl, $C_1$–$C_6$-alkoxy, $C_1$–$C_6$-alkylthio, $C_1$–$C_6$-alkylsulfinyl, $C_1$–$C_6$-alkylsulfonyl, $C_1$–$C_6$-alkylamino, di($C_1$–$C_6$-alkyl)amino, ($C_1$–$C_6$-alkyl)oxycarbonyl, phenyl, phenoxy, 2-, 3- or 4-pyridyl, $R^2$ and $R^5$ are identical or different and independently of one another are
  hydrogen, hydroxyl, $C_1$–$C_6$-alkoxy, aryloxy, $C_1$–$C_6$-acyloxy, cyano, amino, $C_1$–$C_6$-alkylamino, di($C_1$–$C_6$-alkyl)amino, arylamino, $C_1$–$C_6$-acylamino, $C_1$–$C_6$-alkyl,
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
  $C_2$–$C_8$-alkenyl,
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl and carbamoyl;
  $C_3$–$C_8$-allenyl, optionally substituted by fluorine, chlorine or hydroxyl,
  $C_1$–$C_4$-alkoxy, oxo, phenyl;
  $C_3$–$C_8$-alkynyl,
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
  $C_3$–$C_8$-cycloalkyl,
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
  $C_3$–$C_8$-cycloalkenyl,
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
  ($C_3$–$C_8$-cycloalkyl)-($C_1$–$C_4$-alkyl),
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;
  ($C_3$–$C_8$-cycloalkenyl)-($C_1$–$C_4$-alkyl),
  optionally substituted by
    fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_1$–$C_6$-alkylcarbonyl, optionally substituted by fluorine, chlorine, bromine, iodine, cyano, amino, mercapto, hydroxyl, $C_1$–$C_6$-acyloxy, benzoyloxy, benzyloxy, phenoxy, $C_1$–$C_6$-alkoxy, $C_1$–$C_6$-alkylamino, di($C_1$–$C_6$-alkyl)amino, $C_1$–$C_6$-alkylthio, $C_1$–$C_6$-alkylsulfonyl, phenylsulfonyl, oxo, thioxo, carboxyl or carbamoyl;

$C_2$–$C_8$-alkenylcarbonyl, optionally substituted by fluorine, chlorine or hydroxyl, $C_1$–$C_4$-alkoxy, oxo, phenyl;

($C_3$–$C_8$-cycloalkyl)carbonyl, optionally substituted by fluorine, chlorine or hydroxyl, $C_1$–$C_4$-alkoxy, oxo, phenyl;

($C_5$–$C_8$-cycloalkenyl)carbonyl, optionally substituted by fluorine, chlorine or hydroxyl, $C_1$–$C_4$-alkoxy, oxo, phenyl;

($C_3$–$C_8$-cycloalkyl)-($C_1$–$C_3$-alkyl)carbonyl, optionally substituted by fluorine, chlorine or hydroxyl, $C_1$–$C_4$-alkoxy, oxo, phenyl;

($C_5$–$C_6$-cycloalkenyl)-($C_1$–$C_3$-alkyl)carbonyl, optionally substituted by fluorine, chlorine or hydroxyl, $C_1$–$C_4$-alkoxy, oxo, phenyl;

$C_1$–$C_8$-alkyloxycarbonyl, optionally substituted by fluorine, chlorine, bromine, hydroxyl, $C_1$–$C_4$-alkoxy, $C_1$–$C_4$-alkylamino, di($C_1$–$C_4$-alkyl)amino, $C_1$–$C_4$-alkylthio;

$C_2$–$C_8$-alkenyloxycarbonyl, optionally substituted by fluorine, chlorine, hydroxyl, $C_1$–$C_4$-alkoxy, oxo, phenyl;

$C_2$–$C_8$-alkynyloxycarbonyl, optionally substituted by fluorine, chlorine, hydroxyl, $C_1$–$C_4$-alkoxy, oxo, phenyl;

$C_1$–$C_8$-alkylthiocarbonyl, optionally substituted by fluorine, chlorine, hydroxyl, $C_1$–$C_4$-alkoxy, oxo, phenyl;

$C_2$–$C_8$-alkenylthiocarbonyl, optionally substituted by fluorine, chlorine, hydroxyl, $C_4$–$C_4$-alkoxy, oxo, phenyl;

$C_1$–$C_8$-alkylamino- and di($C_1$–$C_8$-alkyl)aminocarbonyl, in each case optionally substituted by fluorine, chlorine, hydroxyl, $C_1$–$C_4$-alkoxy, oxo, phenyl;

pyrrolidin-1-yl, morpholino-, piperidino-, piperazinyl-, or 4-methylpiperazin-1-ylcarbonyl, in each case optionally substituted by $C_1$–$C_4$-alkyl, $C_2$–$C_6$-alkenyl, $C_1$–$C_4$-acyl, oxo, thioxo, carboxyl, or phenyl;

$C_2$–$C_8$-alkenylamino- and di($C_1$–$C_6$-alkenyl)aminocarbonyl, in each case optionally substituted by fluorine, chlorine, hydroxyl, $C_1$–$C_4$-alkoxy, oxo, phenyl;

$C_1$–$C_6$-alkylsulfonyl, optionally substituted by fluorine, chlorine, hydroxyl, $C_1$–$C_4$-alkoxy, oxo, phenyl; $C_1$–$C_6$-alkenylsulfonyl, optionally substituted by fluorine, chlorine, hydroxyl, $C_1$–$C_4$-alkoxy, oxo, phenyl; or aryl, arylcarbonyl, aryl(thiocarbonyl), (arylthio)carbonyl, (arylthio)thiocarbonyl, aryloxycarbonyl, arylaminocarbonyl, (arylamino)thiocarbonyl, arylalkylaminocarbonyl, arylsulfonyl, arylalkyl, arylalkenyl, arylalkynyl, arylalkylcarbonyl, arylalkenylcarbonyl, arylalkoxycarbonyl or aryl(alkylthio)carbonyl, each of which is substituted by up to five radicals $R^6$ which are independent of one another, it being possible for the alkyl radical to contain in each case 1 to 5 carbon atoms, and $R^6$ being as defined above, or heteroaryl, heteroarylalkyl, heteroarylalkenyl, heteroarylalkylcarbonyl or heteroarylalkenylcarbonyl, heteroaryloxycarbonyl, (heteroarylthio)carbonyl, heteroarylaminocarbonyl, heteroarylalkyloxycarbonyl, heteroaryl(alkylthio)carbonyl or heteroarylalkylaminocarbonyl, each of which is substituted by up to three radicals $R^6$ which are independent of one another, it being possible for the alkyl radical to contain in each case 1 to 3 carbon atoms, $R^3$ and $R^4$ are identical or different and, independently of one another, are hydrogen, $C_1$–$C_8$-alkyl which is optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_2$–$C_8$-alkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkyl, optionally substituted by fluorine, chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

$C_3$–$C_8$-cycloalkenyl, optionally substituted by fluorine or chlorine, hydroxyl, amino, mercapto, $C_1$–$C_4$-acyloxy, benzoyloxy, benzyloxy, phenoxy, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl or carbamoyl;

aryl, arylalkyl, heteroaryl or heteroarylalkyl, each of which is substituted by up to five radicals $R^6$ which are independent of one another, it being possible for the alkyl radical to contain 1 to 3 carbon atoms in each case, and $R^6$ being as defined above, $R^3$ and $R^4$ or $R^3$ and $R^5$ can furthermore also be part of a saturated or unsaturated carbo- or heterocyclic ring which has 3 to 8 carbon atoms and which can optionally be substituted by fluorine, chlorine, hydroxyl, amino, $C_1$–$C_6$-alkyl, $C_2$–$C_6$-alkenyl, $C_2$–$C_6$-alkynyl, $C_1$–$C_6$-acyloxy, benzoyloxy, $C_1$–$C_6$-alkoxy, oxo, thioxo, carboxyl, carbamoyl or phenyl, X is oxygen, sulfur, selenium or substituted nitrogen N—$R^2$, it being possible for $R^2$ to have the abovementioned meanings, for the preparation of pharmaceuticals for the treatment of viral diseases.

The compounds mentioned and elucidated above under 1)–4) are preferred for this use.

The pharmaceuticals according to the invention can be administered enterally (orally), parenterally (intravenously), rectally, subcutaneously, intramuscularly or locally (topically).

They can be administered in the form of solutions, powders, (tablets, capsules including microcapsules), ointments (creams or gels) or suppositories. Suitable adjuvants for such formulations are the liquid or solid fillers and extenders, solvents, emulsifiers, glidants, flavorings, colorings and/or buffer substances which are customary in pharmacology.

0.1–10, preferably 0.2–8 mg/kg of body weight are administered once or several times daily as an expedient dosage. The dosage units used depend expediently on the specific pharmacokinetics of the substance used, or on the pharmaceutical formulation used.

For example, the dosage unit of the compounds according to the invention is 1–1500 mg, preferably 50–500 mg.

The compounds according to the invention can also be administered as a combination with other antiviral agents such as, for example, nucleoside analogs, protease inhibitors or adsorption inhibitors, immunostimulants, interferons, interleukins and colony-stimulating factors (for example GM-CSF, G-CSF, M-CSF).

ACTIVITY TESTS

Test of Preparations Against HIV in Cell Culture

Description of Method

Medium:

RMPI pH 6.8

Complete medium additionally contains 20% fetal calf serum and 40 IU/ml recombinant interleukin 2.

Cells:

Lymphocytes which have been isolated from fresh donor blood by means of Ficoll gradient centrifugation are cultured for 36 hours in complete medium with an addition of 2 µg/ml phytohemagglutinin (Wellcome) at 37° C. under 5% of $CO_2$. After 10% of DMSO has been added, the cells are frozen at a density of 5 ■ $10^6$ and stored in liquid nitrogen. For the test, the cells are defrosted, washed in RPMI medium and cultured for 3–4 days in the complete medium.

Mixture:

The test preparations were dissolved in DMSO at a concentration of 16.7 mg/ml and diluted in complete medium to 1 mg/ml.

0.4 ml of medium was introduced into 24-multiwell dishes. 0.1 ml of the dissolved preparation was added to the upper row of the dish, and, by transferring 0.1 ml portions, a geometric dilution series was established. Controls without preparation always contained 0.4 ml of complete medium containing 0.5% of DMSO. Lymphocyte cultures with a cell density of 5 ■ $10^5$ cells/ml were infected by adding 1/50 volume supernatant from HIV-infected lymphocyte cultures. The titer of these culture supernatants was determined by end-point titration as 1–5 ■ $10^6$ infectious units/ml. After 30 minutes' incubation at 37° C., the infected lymphocytes were removed by centrifugation and taken up in an equal volume of medium. From this cell suspension, 0.6 ml aliquots were transferred into all wells of the test plate. The mixtures were incubated for 3 days at 37° C.

Evaluation:

The infected cell cultures were examined under the microscope for the presence of giant cells, which indicate active virus multiplication in the culture. The lowest concentration of preparation where no giant cells were observed was determined as inhibitory concentration against HIV. As a control, the supernatants from the culture plates were tested for the presence of HIV antigen with the aid of an HIV antigen test following the manufacturer's instructions (Organon).

Results:

The results from this test are shown in Table 1.

| Compound of Example No. | T-cell culture assay MIC (µg/ml) |
| --- | --- |
| III | 0.8 |
| IV | >0.8 |
| VI-A | 0.16 |
| VI-B | 20 |
| VI-C | <0.8 |
| VII | <0.16 |
| X | 0.8 |
| XII | <0.8 |
| XIII | <0.16 |
| XIV | <0.16 |
| 3-7 | 0.08 |
| 3-21 | 0.16 |
| 3-23 | 0.08 |
| 3-24 | 0.08 |
| 3-25 | 0.4 |
| 3-26 | 0.4 |
| 3-29 | <0.4 |
| 3-30 | <0.01 |
| 3-32 | <0.4 |
| 3-33 | 0.4 |
| 3-36 | <2.0 |
| 3-44 | <0.8 |
| 3-48 | <0.8 |
| 3-49 | <0.8 |
| 3-52 | >0.8 |
| 3-53 | >0.8 |
| 3-57 | <0.8 |
| 3-62 | <4.0 |
| 3-64 | >0.8 |
| 3-66 | >0.08 |
| 3-67 | <0.8 |
| 3-73 | >0.4 |
| 3-75 | <0.8 |
| 3-76 | <0.08 |
| 3-80 | 0.4 |
| 3-81 | 0.08 |
| 3-87 | >0.8 |
| 3-88 | 0.8 |
| XX | <4.0 |
| 6-1 | 0.4 |
| 6-16 | <0.8 |
| 6-17 | <0.8 |
| 6-19 | <0.8 |
| 6-20 | <0.8 |
| 6-22 | >0.8 |
| 6-27 | <0.4 |
| 6-32 | <0.08 |
| 6-33 | >0.8 |
| 6-34 | <0.4 |
| 6-35 | <0.08 |
| 6-36 | <0.8 |
| 6-39 | 0.4 |
| 6-41 | <20 |
| 6-50 | <0.01 |
| XXIII | <0.01 |
| 7-1 | <0.16 |
| 7-2 | <0.01 |
| 7-3 | <0.01 |
| 7-7 | 0.04 |
| 7-10 | <0.04 |
| 7-11 | <0.01 |
| 7-12 | <0.8 |
| 7-13 | <0.08 |
| 7-14 | <0.08 |
| 7-16 | 0.4 |
| 7-21 | <0.01 |
| 7-22 | <0.01 |
| 7-23 | <0.01 |
| 10-4 | 0.4 |
| 10-5 | <0.8 |
| 10-9 | <0.8 |
| 10-10 | 0.08 |
| 10-13 | 0.08 |

| Compound of Example No. | T-cell culture assay MIC ($\mu$g/ml) |
| --- | --- |
| 10-14 | <0.8 |
| 10-17 | 0.8 |
| 10-18 | <0.8 |
| 10-20 | <0.8 |
| 10-21 | <0.8 |
| 10-27 | 0.8 |
| 10-28 | <0.8 |
| 11-1 | <0.8 |
| 11-2 | >0.8 |
| 11-3 | <0.8 |
| 11-4 | 0.8 |
| 11-11 | 0.01 |

Assay of the Substances for HIV Reverse Transcriptase Inhibition

The activity of reverse transcriptase (RT) was determined with the aid of a scintillation proximity assay (SPA).

The reagent kit for the RT-SPA was obtained from Amersham/Buchler (Braunschweig).

The enzyme RT (from HIV cloned in *E. coli*) originated from HT-Biotechnology Ltd, Cambridge, UK.

Mixture

The assay was carried out using the manufacturer's (Amersham) protocol manual, with the following modifications:

- bovine serum albumin was added to the assay buffer to give an end concentration of 0.5 mg/ml
- the assay was carried out in Eppendorf reaction vessels, using 100 $\mu$l volume per batch
- the manufacturer's RT concentrate (5000 U/ml) was diluted in Tris-HCl buffer 20 mM; pH 7.2; 30% of glycerol, to an activity of 15 U per ml
- the incubation time for the mixtures was 60 minutes (37° C.)
- after stopping the reaction and "developing" with the bead suspension, 130 $\mu$l of mixture were transferred to 4.5 ml of Tris-HCl buffer, 10 mM; pH 7.4; 0.15 M NaCl, and the tritium activity was measured by means of a $\beta$-counter.

Assay

For a pre-assay for inhibitory activity, the substances were dissolved in DMSO (stock solution c=1 mg/ml), and tested as a $10^{-1}$, $10^{-2}$, $10^{-3}$, etc., dilution in DMSO.

To determine IC$_{50}$ values, the inhibitor stock solutions were diluted further in Tris-HCl buffer, 50 mM, pH 8, and tested in suitable concentrations.

The concentration corresponding to a 50% enzyme inhibition was determined from a plot of RT activity versus log C$_i$nh.

The test results are shown in Table 1a.

TABLE 1a

| Compound of Example No. | Reverse Transcriptase Assay IC$_{50}$ ($\mu$g/ml) |
| --- | --- |
| V | 7.5 |
| VI-A | 0.08 |
| VI-C | 0.8 |
| VII | 0.1 |
| XIII | 0.04 |
| XIV | 0.16 |
| 3-23 | 0.1–1 |
| 3-24 | 0.1–1 |
| 3-25 | 0.1–1 |
| 3-29 | 0.1–1 |
| 3-30 | 0.025 |
| 3-32 | approx. 0.1 |
| 3-36 | 0.1–1 |
| 3-49 | approx. 1 |
| 3-57 | approx. 1 |
| 3-75 | 0.1–1 |
| 3-76 | 0.018 |
| 3-81 | approx. 1 |
| 6-1 | approx. 1 |
| 6-8 | 0.1–1 |
| 6-9 | approx. 1 |
| 6-16 | approx. 1 |
| 6-17 | 0.1–1 |
| 6-27 | approx. 1 |
| 6-35 | 0.1–1 |
| 6-50 | 0.01–0.1 |
| XXIII | 0.025 |
| 7-1 | 0.08 |
| 7-2 | 0.07 |
| 7-3 | 0.07 |
| 7-7 | 0.1 |
| 7-10 | 0.11 |
| 7-11 | 0.01 |
| 7-12 | approx. 1 |
| 7-13 | 0.1–1 |
| 7-16 | approx. 1 |
| 10-9 | approx. 1 |
| 10-10 | approx. 1 |
| 10-13 | approx. 1 |
| 10-17 | approx. 1 |
| 10-18 | 0.1–1 |
| 10-20 | 0.1–1 |
| 10-21 | 0.1–1 |
| 10-27 | 0.1–1 |
| 10-28 | 0.1–1 |
| 11-11 | 0.1–1 |
| 10-34 | 0.1–1 |
| 11-6 | 0.1–1 |
| 11-5 | 0.1–1 |
| 11-7 | approx. 1 |
| 11-13 | approx. 1 |
| 7-20 | 0.1–1 |
| 7-14 | 0.01–0.1 |
| 7-15 | 0.01–0.1 |
| 7-17 | 0.01–0.1 |
| 7-18 | 0.01–0.1 |
| 7-19 | 0.01–0.1 |
| 7-21 | 0.01–0.1 |
| 7-22 | 0.01–0.1 |
| 7-23 | 0.01–0.1 |
| 3-34 | 0.1–1 |
| 3-35 | 0.1–1 |
| 3-37 | 0.1–1 |
| 3-7 | 0.08 |
| 3-127 | 0.01–0.1 |
| 3-128 | 0.01–0.1 |
| 3-129 | 0.01–0.1 |
| 7-24 | <0.01 |
| 7-25 | <0.01 |
| 7-26 | 0.01–0.1 |
| 7-27 | 0.1–1 |
| 7-28 | <0.01 |
| 7-29 | 0.01–0.1 |
| 7-30 | <0.01 |
| 7-31 | <0.01 |

IC$_{50}$ = 0.08 $\mu$g/ml

The examples which follow and the content of the patent claims illustrate the present invention in greater detail.

EXAMPLE I (3S)-6-Chloro-3-methyl-3,4-dihydroquinoxalin-2 (1H)-one

A) (S)-N-(3-Chloro-6-nitrophenyl)alanine 2,4-Dichloronitrobenzene (21.0 g, 0.109 mol) and 23.0 g (0.258 mol) of L-alanine were refluxed for 48 hours in 400 ml of 2-methoxyethanol with an addition of 120 ml of 2N sodium hydroxide solution. The mixture was subsequently concentrated in vacuo, and the residue was taken up in aqueous sodium hydrogen carbonate solution. The mixture was extracted three times using ethyl acetate, the extract was then acidified with 6N hydrochloric acid, and the yellow product was extracted using ethyl acetate. The organic phase was washed once with saturated aqueous sodium chloride solution and dried (magnesium sulfate), and the solvent was removed under reduced pressure. 14.7 g (55%) of a yellow solid of melting point 167–169° C. remained (after crystallization from ethyl acetate).

$^1$H NMR (270 MHz, $d_6$-DMSO): δ=1.47 (d, J=7 Hz, 3 H), 4.57 (quintet, J=7 Hz, 1 H), 6.77 (dd, J=9, 2 Hz, 1 H), 7.11 (d, J=2 Hz, 1 H), 8.12 (d, J=9 Hz, 2 H), 8.41 (br. d, J=7 Hz, 1 H), 13.2 ppm (br., 1 H). MS: (M+H)$^+$=245.

B) (3S)-6-Chloro-3-methyl-3,4-dihydroquinoxalin-2(1H)-one

The product of Example IA (14.0 g, 0.057 mol) was dissolved in 400 ml of methanol and hydrogenated with Raney nickel catalysis at room temperature, using 1 atm hydrogen. After the calculated amount of hydrogen had been taken up, the catalyst was removed by filtration with suction, and the reaction solution was concentrated in vacuo. The residue was purified by silica gel chromatography using ethyl acetate/heptane=1:2 and 1:1 as the eluent. The yield was 6.0 g (53%) of a brownish solid of melting point 122–123° C. (after recrystallization from isopropanol/heptane).

$^1$H NMR (60 MHz, $d_6$-DMSO): δ=1.23 (d, J=11 Hz, 3 H), 3.81 (dq, J=11, 4 Hz, 1 H), 6.27 (br., 1 H), 6.3–6.9 (m, 3 H), 10.3 ppm (br., 1 H). MS: (M+H)$^+$=197; $[α]_D^{23}$=+77.3° (c=1, MeOH)

C) (3R)-6-Chloro-3-methyl-3,4-dihydroquinoxalin-2(1H)-one

The compound was prepared from D-alanine by the methods described under Example IA and IB. Melting point 123–124° C. (after recrystallization from isopropanol/heptane)

The NMR data agree with those of the compound described in Example IB. $[α]_D^{23}$=−81.0° (c=1, MeOH)

D) (3RS)-6-Chloro-3-methyl-3,4-dihydroquinoxalin-2(1H)-one

The compound was prepared starting from D,L-alanine by the methods described in Examples IA and IB. Melting point 110° C. (after recrystallization from isopropanol/heptane)

The NMR data agree with those of the compound described in Example IB.

The following compounds of the formula I were synthesized analogously using the corresponding haloaromatic compounds and amino acid derivatives:

EXAMPLE II (3S)-3-Benzyl-7-chloro-3,4-dihydroquinoxalin-2 (1H)-one

A) (S)-N-(4-chloro-2-nitrophenyl)-phenylalanine

L-Phenylalanine (8.3 g, 0.05 mol) and 4.8 g (0.025 mol) of 2,5-dichloronitrobenzene were dissolved in 40 ml of anhydrous dimethyl sulfoxide (DMSO), and the stirred solution was heated to 80° C. under an argon atmosphere. Potassium tert.-butylate (4.2 g, 0.025 mol), dissolved in 30 ml of DMSO, was added dropwise in the course of 40 minutes. Stirring was continued for 3 hours at 80 to 90° C., the mixture was allowed to cool, and unreacted phenylalanine was removed by filtration with suction and washed with water. The collected alkaline filtrates were extracted twice using diethyl ether to remove unreacted dichloronitrobenzene. The mixture was then acidified using glacial acetic acid and extracted several times using ethyl acetate, and the extracts were dried over magnesium sulfate and evaporated.

The product was obtained in the form of a red oil (6.7 g, 84%), which was further reacted without purification.

B) (3S)-3-Benzyl-7-chloro-3,4-dihydroquinoxalin-2(1H)-one

The product of Example IIA (12 g) was dissolved in 300 ml of anhydrous methanol and hydrogenated at room temperature with palladium/charcoal catalysis, using 1 atm hydrogen. When the reaction had ended, solids were filtered off with suction, the liquid was concentrated, and the concentrate was chromatographed on silica gel using diisopropyl ether as the eluent. This gave 1.32 g of the desired product which crystallized from isopropanol, melting point 185°.

$^1$H NMR (270 MHz, $d_6$-DMSO): δ=2.9 (m, 2 H), 4.08 (m, 1 H), 6.09 (d, 1 H), 6.7 (m, 2 H), 6.78 (m, 1 H), 7.2 (m, 5 H), 10.34 ppm (br. s, 1 H). MS: (M+H)$^+$=273, (M−92)$^+$=181.

The compounds in Table 2 were prepared as described in the above examples.

TABLE 2

| Nr. | $R^1_n$ | $R^3$ | $R^5$ | M.P.° C. |
|---|---|---|---|---|
| 1 | 5-Cl | $CH_3$ | H | Wax |
| 2 | 6-Cl | $C_2H_5$ | H | 120 |
| 3 | 6-Cl | $C_2H_4COOH$ | H | |
| 4 | 6-Cl | —$CH_2CH_2CO$— | | |
| 5 | 6-Cl | $(CH_3)_2CH$ | H | |
| 6 | 6-Cl | $(CH_3)_2CHCH_2$ | H | Oil |
| 7 | 6-Cl | $C_2H_5(CH_3)CH$ | H | Oil |
| 8 | 6-Cl | $C_6H_5CH_2$ | H | 156–157 |
| 9 | 6-Cl | $CH_3SCH_2CH_2$ | H | 97 |
| 10 | 6-Cl | $CH_3SCH_2$ | H | 149 |
| 11 | 6-Cl | $CH_2(OH)$ | H | |
| 12 | 6-Cl | $CH_3CH_2CH_2$ | H | 75–77 |
| 13 | 7-Cl | $CH_3$ | H | 142 |
| 14 | 7-Cl | $(CH_3)_2CH$ | H | Oil |
| 15 | 7-Cl | $CH_3SC_2H_4$ | H | 98 |
| 16 | 8-Cl | $CH_3$ | H | |
| 17 | 6,7-$Cl_2$ | $CH_3$ | H | |
| 18 | 7-F | $CH_3$ | H | 230 |
| 19 | 6-F | $CH_3$ | H | Wax |
| 20 | 6-F | $CH_3$ | $C_3H_5$ | 182 |
| 21 | 6-F | $C_6H_5CH_2$ | $C_3H_6$ | |
| 22 | 7-$CF_3$ | $CH_3$ | H | 147 |
| 23 | 6-$CH_3OC_2H_4O$ | $C_2H_5$ | H | 107 |
| 24 | 6-Cl | $C_2H_4OH$ | H | 211 |
| 25 | 6-Cl | $CH_2$—S—Bn | H | 170 |
| 26 | 6-Cl | $CH_2$—S—i.-Pr | H | 190 |

TABLE 2-continued

[Structure: quinoxalin-2(1H)-one core with $R^1_n$ on benzene ring, $R^3$ at 3-position, $R^5$ on N]

| Nr. | $R^1_n$ | $R^3$ | $R^5$ | M.P.° C. |
|---|---|---|---|---|
| 27 | 6-Cl | CH$_2$O—t.-Bu | H | 128 |
| 28 | 6-Cl | C$_4$H$_9$ | H | 115 |

Bn = benzyl
i-Pr = isopropyl
t-Bu = tert.-butyl

EXAMPLE III (3S)-4-N-(Benzyloxycarbonyl)-6-chloro-3-methyl-3,4-di-hydroquinoxalin-2(1H)-one The compound of Example IB (1.0 g, 5.1 mmol) was dissolved in 20 ml of dichloromethane. 10 ml of 2N aqueous sodium hydrogen carbonate solution were added, and 0.9 ml (90%; 5.7 mmol) of benzyl chloroformate was added with ice-cooling and vigorous stirring. The two-phase system was subsequently stirred for 60 hours at room temperature. After 30 hours, another 0.2 ml (1.3 mmol) of benzyl chloroformate was added. When the reaction was complete, the phases were separated, the organic phase was washed once with water and dried (magnesium sulfate), and the solvent was removed in vacuo. The product was purified by silica gel chromatography with methyl tert.-butyl ether/heptane=1:1 as the eluent. This gave 1.65 g (98%) of a white, foam-like product.

$^1$H NMR (270 MHz, d$_6$-DMSO): δ=1.15 (d, J=7 Hz, 3 H), 4.85 (q, J=7 Hz, 1 H), 5.20 (d, J=12 Hz, 1 H), 5.27 (d, J=12 Hz, 1 H), 6.97 (d, J=7 Hz, 1 H), 7.19 (dd, J=8.2 Hz, 1 H), 7.3–7.45 (m, 5 H), 7.67 (d, J=2 Hz, 1 H), 10.81 ppm (br. s, 1 H). MS: (M+H)$^+$=381.

EXAMPLE IV (3S)-4-N-(Benzyloxycarbonyl)-6-chloro-3-methyl-8-nitro-3,4-dihydroquinoxalin-2(1H)-one The compound of Example III (1.5 g, 4.5 mmol) was nitrated in glacial acetic acid (15 ml). A total of 5 ml (124.3 mmol) of fuming nitric acid were added dropwise in the course of 4 hours at 0° C. to room temperature. The mixture was subsequently poured into 100 ml of ice-water, and the product, which was obtained in the form of a yellow solid, was filtered off, washed thoroughly with water, and dried. Melting point 85° C. (subl.).

$^1$H NMR (270 MHz, d$_6$-DMSO): δ=1.22 (d, J=8 Hz, 3 H), 4.89 (q, J=8 Hz, 1 H), 5.24 (d, J=12 Hz, 1 H), 5.31 (d, J=12 Hz, 1 H), 7.35–7.5 (m, 5 H), 7.69 (s, 1 H), 8.00 (s, 1 H), 11.11 ppm (br. s, 1 H). MS: (M+H)$^+$=376.

EXAMPLE V (3S)-8-Amino-4-N-(benzyloxycarbonyl)-6-chloro-3-methyl-3,4-dihydroquinoxalin-2(1H)-one The compound of Example IV (1.5 g, 4.0 mmol) was dissolved in 150 ml of methanol and hydrogenated at room temperature with Raney nickel catalysis, using 1 atm hydrogen. When the calculated amount of hydrogen had been taken up, the catalyst was removed by filtration with suction, and the filtrate was concentrated in vacuo. The product was purified by silica gel chromatography using ethyl acetate/heptane=2:1 as eluent. The yield was 0.68 g (49%) of brownish solid of melting point 152–154° C.

$^1$H NMR (270 MHz, d$_6$-DMSO): δ=1.11 (d, J=8 Hz, 3 H), 4.79 (q, J=8 Hz, 1 H), 5.15 (d, J=12 Hz, 1 H), 5.24 (d, J=12 Hz, 1 H), 5.38 (br. s, 2 H), 6.42 (s, 1 H), 7.3–7.4 (m, 6 H), 10.59 ppm (br. s, 1 H). MS: (M+H)$^+$=346.

EXAMPLE VI

A) (3S)-6-Chloro-3-methyl-4-N-(3-methyl-2-buten-1-yl)-3,4-dihydroquinoxalin-2(1H)-one The compound of Example IB (1.0 g, 5.0 mmol) was dissolved in 20 ml of acetonitrile and alkylated with 3-methyl-2-buten-1-yl bromide (90%; 0.92 ml, 7.0 mmol) at room temperature in the presence of 1.0 g (7.0 mmol) of pulverulent potassium carbonate. After 7 hours, the reaction had ended. The mixture was filtered off with suction, the filtrate was concentrated in vacuo, and the product was purified by silica gel chromatography using ethyl acetate/heptane=1:2 as eluent. The yield was 0.97 g (72%) of brownish solid of melting point 117–118° C. (after crystallization from methyl tert.-butyl ether/heptane).

$^1$H NMR (270 MHz, d$_6$-DMSO): δ=1.02 (d, J=8 Hz, 3 H), 1.74 (s, 6 H), 3.69 (dd, J=14, 8 Hz, 1 H), 3.85–3.9 (m, 2 H), 5.19 (m, 1 H), 6.65–6.8 (m, 3 H), 10.47 ppm (br. s, 1 H). MS: (M+H)$^+$=265; [α]$_D^{23}$=+168.0° (c=1, MeOH).

B) (3R)-6-Chloro-3-methyl-4-N-(3-methyl-2-buten-1-yl)-3,4-dihydroquinoxalin-2(1H)-one The compound was prepared by the method described in Example VIA, starting from the compound of Example IC. Melting point 115–117° C. (after recrystallization from isopropanol/diethyl ether).

The NMR data agreed with those of the compound described in Example VIA. [α]$_D^{23}$=−172° (c=1, MeOH).

C) (3RS)-6-Chloro-3-methyl-4-N-(3-methyl-2-buten-1-yI)-3,4-dihydroquinoxalin-2(1H)-one The compound was prepared by the method described in Example VIA starting with the compound of Example ID. Melting point 148–149° C. (after recrystallization from isopropanol/diethyl ether)

The NMR data agreed with those of the compound described in Example VIA.

EXAMPLE VII (3S)-6-Chloro-3-methyl-4-N-(2-buten-1-yl)-3,4-dihydroquinoxalin-2(1H)-one The substance was prepared analogously to the compound described in Example VIA, but with 2-buten-1-yl bromide as the alkylating agent. Melting point 87–88° C. (after crystallization from diethyl ether/heptane)

$^1$H NMR (270 MHz, d$_6$-DMSO): δ=1.01 (d, J=8 Hz, 3 H), 1.70 (dd, J=8, 1 Hz, 3 H), 3.63 (dd, J=16, 6 Hz, 1 H), 3.85–4.0 (m, 2 H), 5.47 (m, 1 H), 5.75 (m, 1 H), 6.65–6.8 (m, 3 H), 10.48 ppm (br. s, 1 H). MS: (M+H)$^+$=251.

EXAMPLE VIII

4-N-(Isopropenyloxycarbonyl)-3,3,7-trimethyl-3,4-di-hydroquinoxalin-2(1H)-one 3,3,7-Trimethyl-3,4-dihydroquinoxalin-2(1H)-one (0.4 g, 2.1 mmol) were dissolved in 10 ml of anhydrous pyridine, and the stirred solution was treated at room temperature with 0.24 ml (2.2 mmol) of isopropenyl chloroformate. The mixture was stirred for 6 hours at room temperature and treated with water, the precipitate which formed was filtered off with suction, washed with water and dried. This gave 0.4 g (69%) of colorless crystals of melting point 185° C.

$^1$H NMR (270 MHz, d$_6$-DMSO): δ=1.5 (s, 6 H), 1.9 (s, 3 H), 2.25 (s, 3 H), 4.7 (m, 2 H), 6.7–6.9 (m, 2 H), 7.15 (d, J=8 Hz, 1 H), 10.6 ppm (br. s, 1 H). MS: $^+$=274.

EXAMPLE IX (3S)-6-Chloro-4-N-(4-methoxyphenoxycarbonyl)-3-methyl-3,4-dihydroquinoxalin-2(1H)-one The compound of Example IB (0.5 g, 2.55 mmol) was dissolved in 10 ml of anhydrous N,N-dimethylformamide, and 0.41 ml (2.8 mmol) of triethylamine were added. To the stirred mixture there was first added dropwise 0.42 ml (2.8 mmol) of 4-methoxyphenyl chloroformate and, after 2 hours, another 0.21 ml (1.9 mmol). When the reaction was complete (18 hours), the solvent was stripped off under reduced pressure, the residue was taken up in ethyl acetate, and the mixture was washed with water and dried (sodium sulfate). 0.48 g (54%) of a white solid remained after concentration. Melting point 187–190° C. (after recrystallization from isopropanol).

$^1$H NMR (270 MHz, d$_6$-DMSO): δ=1.24 (d, J=8 Hz, 3 H), 3.77 (s, 3 H), 4.94 (q, J=8 Hz, 1 H), 6.97 (dd, J=8, 2 Hz, 1 H), 7.03 (d, J=8 Hz, 1 H), 7.2–7.3 (m, 3 H), 7.78 (s, 1 H), 10.89 ppm (br. s, 1 H). MS: (M+H)$^+$=347.

EXAMPLE X (3S)-6-Chloro-4-N-(4-fluorophenoxycarbonyl)-3-methyl-3,4-dihydroquinoxalin-2(1H)-one The compound was prepared analogously to the compound described in Example VIA, but 4-fluorophenyl chloroformate was used as acylating agent. Melting point 168–170° C. (after crystallization from isopropanol).

$^1$H NMR (270 MHz, d$_6$-DMSO): δ=1.24 (d, J=8 Hz, 3 H), 4.94 (q, J=8 Hz, 1 H), 7.03 (d, 8 Hz, 1 H), 7.2–7.5 (m, 5 H), 7.83 (d, J=2 Hz, 1 H), 10.90 ppm (br. s, 1 H). MS: (M+H)$^+$=335.

EXAMPLE XI (3S)-6-Chloro-4-N-(4-chlorophenoxycarbonyl)-3-methyl-3,4-dihydroquinoxalin-2(1H)-one The compound was prepared analogously to the compound described in Example VIA, but 4-chlorophenyl chloroformate was used as acylating agent. Melting point 185–188° C. (after crystallization from isopropanol/diethyl ether).

$^1$H NMR (270 MHz, d$_6$-DMSO): δ=1.25 (d, J=8 Hz, 3 H), 4.94 (q, J=8 Hz, 1 H), 7.04 (d, 8 Hz, 1 H), 7.25 (dd, J=8, 2 Hz, 1 H), 7.35–7.6 (m, 4 H), 7.80 (s, 1 H), 10.91 ppm (br. s, 1 H). MS: (M+H)$^+$=351.

EXAMPLE XII (3S)-4-N-(2-Bromoethyloxycarbonyl)-6-chloro-3-methyl-3,4-dihydroquinoxalin-2(1H)-one The compound was prepared analogously to the compound described in Example VIA, but 2-bromoethyl chloroformate was used for the acylation. Melting point 133–136° C. (after crystallization from isopropanol).

$^1$H NMR (270 MHz, d$_6$-DMSO): δ=1.16 (d, J=8 Hz, 3 H), 3.7–3.8 (m, 2 H), 4.4–4.6 (m, 2 H), 4.86 (q, J=8 Hz), 6.99 (d, 8 Hz, 1 H), 7.21 (dd, 8, 2 Hz, 1 H), 7.74 (d, J=2 Hz, 1 H), 10.84 ppm (br. s, 1 H). MS: (M+H)$^+$=348.

EXAMPLE XIII (3S)-6-Chloro-N-(isopropenyloxycarbonyl)-3-methyl-3,4-dihydroquinoxalin-2(1H)-one The substance was prepared analogously to the compound described in Example VIA, but isopropenyl chloroformate was used for the acylation. Melting point 158–159° C.

$^1$H NMR (270 MHz, CDCl$_3$): δ=1.33 (d, J=8 Hz, 3 H), 2.02 (s, 3 H), 4.79 (s, 1 H), 4.83 (s, 1 H), 5.17 (q, J=8 Hz, 1 H), 6.86 (d, J=8 Hz, 1 H), 7.12 (dd, J=8, 2 Hz, 1 H), 7.74 (br. s, 1 H), 9.28 ppm (br. s, 1 H). MS: (M+H)$^+$=281.

EXAMPLE XIV (3S)-6-Chloro-3-methyl-4-N-(vinyloxycarbonyl)-3,4-di-hydroquinoxalin-2(1H)-one The substance was prepared analogously to the compound described in Example VIA, but vinyl chloroformate was used for the acylation. Melting point 177–179° C.

$^1$H NMR (270 MHz, CDCl$_3$): δ=1.33 (d, J=8 Hz, 3 H), 4.96 (dd, J=14, 2 Hz, 1 H), 5.20 (q, J=8 Hz, 1 H), 6.83 (d, J=8 Hz, 1 H), 7.12 (dd, J=8, 2 Hz, 1 H), 7.2–7.3 (m, 2 H), 7.71 (br. s, 1 H), 9.42 ppm (br. s, 1 H). MS: (M+H)$^+$=267.

EXAMPLE XV and EXAMPLE XVI

6-Chloro-3,4-dihydroquinoxalin-2(1H)-one was reacted with 3-methyl-2-buten-1-yl bromide analogously to the process described in Example VIA. It was possible to isolate two products by silica gel chromatography.

6-Chloro-4-N-(3-methyl-2-buten-1-yl)-3,4-dihydro-quinoxalin-2(1H)-one Melting point 150–151° C. (after recrystallization from ethyl acetate).

$^1$H NMR (270 MHz, d$_6$-DMSO): δ=1.72 (s, 6 H), 3.67 (s, 2 H), 3.80 (d, J=7 Hz, 2 H), 5.20 (m, 1 H), 6.7–6.8 (m, 3 H), 10.49 ppm (br. s, 1 H). MS: (M+H)$^+$=251.

6-Chloro-4-N-(3-methyl-2-buten-1-yl)-3-(1,1-dimethyl-2-propen-1-yl)-3,4-dihydroquinoxalin-2(1H)-one Melting point 110–112° C. (after crystallization from heptane).

$^1$H NMR (270 MHz, d$_6$-DMSO): δ=0.94 (s, 3 H), 0.97 (s, 3 H), 1.65 (s, 3 H), 1.66 (s, 3 H), 3.77 (dd, J=16, 7 Hz, 1 H), 4.23 (dd, J=16, 7 Hz, 1 H), 4.8–4.9 (m, 2 H), 5.02 (m, 1 H), 5.75 (dd, J=17, 11 Hz, 1 H), 6.6–6.7 (m, 3 H), 10.49 ppm (br. s, 1 H). MS: (M+H)$^+$=319.

The following compounds of the formula I were synthesized from the corresponding unsubstituted quinoxalinones in analogous manner and, if appropriate, derivatized further:

TABLE 3

[Structure: quinoxalin-2-one derivative with R¹ₙ on benzene ring, R² on N1, R³ on C3 (with H), R⁵ on N4]

| Nr. | R¹ₙ | R² | R³ | R⁵ | M.P. °C. |
|---|---|---|---|---|---|
| 1 |  | H | $CH_3$ | $C_2H_4OCH_3$ | 59 |
| 2 |  | H | $CH_3$ | $C_4H_7$ | 110 |
| 3 |  | H | $CH_3$ | $sC_6H_{11}$ | 100 |
| 4 | 5-Cl | H | $CH_3$ | $C_6H_{11}$ | Oil |
| 5 | 5-Cl | H | $CH_3$ | $sC_6H_{11}$ | 135 |
| 6 | 6-Cl | H | $CH_3$ | ALAC | 180–182 |
| 7 | 6-Cl | H | $CH_3$ | ALOC | 124–127 |
| 8 | 6-Cl | H | $CH_3$ | $SO_2CH_3$ | 184 |
| 9 | 6-Cl | H | $CH_3$ | $SO_2C_6H_5$ | 253 |
| 10 | 6-Cl | H | $CH_3$ | $SO_2C_6H_4$-4-$CH_3$ | 259–262 |
| 11 | 6-Cl | H | $CH_3$ | $SO_2C_6H_4$-4-Cl | >270 |
| 12 | 6-Cl | H | $CH_3$ | $SO_2C_6H_4$-4-$NO_2$ | >270 |
| 13 | 6-Cl | H | $CH_3$ | $SO_2CH=CH_2$ | 180–182 |
| 14 | 6-Cl | H | $CH_3$ | $COCH_2OCH_3$ | 202 |
| 15 | 6-Cl | H | $CH_3$ | $CSNH-C_6H_4$-4-CN | 216 |
| 16 | 6-Cl | H | $CH_3$ | $COCH_2CH(CH_3)_2$ | Foam |
| 17 | 6-Cl | H | $CH_3$ | $COC_6H_5$ | 108–109 |
| 18 | 6-Cl | H | $CH_3$ | COCl | 138 |
| 19 | 6-Cl | H | $CH_3$ | $COCH_2CH_2CH=CH_2$ | Foam |
| 20 | 6-Cl | H | $CH_3$ | $C_2H_4OCH_3$ | 78–79 |
| 21 | 6-Cl | H | $CH_3$ | $CH_2C_6H_5$ | 155–156 |
| 22 | 6-Cl | H | $CH_3$ | 2-CO—$C_4H_3O$ | 105–107 |
| 23 | 6-Cl | H | $CH_3$ | $COOCH_2CH_3$ | 149–153 |
| 24 | 6-Cl | H | $CH_3$ | $COO(CH_2)_2CH_3$ | 113–116 |
| 25 | 6-Cl | H | $CH_3$ | $COO(CH_2)_3CH_3$ | 80–82 |
| 26 | 6-Cl | H | $CH_3$ | $COOCH_2CH(CH_3)_2$ | 131–132 |
| 27 | 6-Cl | H | $CH_3$ | $COCH_2CH=CH_2$ | 130 |
| 28 | 6-Cl | H | $CH_3$ | $COCH_2CH=CHCH_3$ | 155 |
| 29 | 6-Cl | H | $C_2H_5$ | $C_5H_9$ | 128 |
| 30 | 6-Cl | H | $C_2H_5$ | IPOC | 175 |
| 31 | 6-Cl | H | $C_2H_5$ | CHO | 204 |
| 32 | 6-Cl | H | $C_2H_5$ | ALOC | 148–150 |
| 33 | 6-$CH_3OC_2H_4O$ | H | $C_2H_5$ | IPOC | 173 |
| 34 | 6-Cl | H | $C_3H_7$ | IPOC | 149–150 |
| 35 | 6-Cl | H | $C_3H_7$ | ALOC | 135 |
| 36 | 6-Cl | H | $CH(CH_3)_2$ | $C_5H_9$ | 126–128 |
| 37 | 6-Cl | H | $CH(CH_3)_2$ | IPOC | 144–145 |
| 38 | 6-Cl | H | $CH(CH_3)_2$ | ALOC |  |
| 39 | 6-Cl | H | $C_2H_4COOH$ | $C_5H_9$ |  |
| 40 | 6-Cl | H | $C_4H_9$ | $C_5H_9$ |  |
| 41 | 6-Cl | H | $CH_2C_6H_5$ | $C_5H_9$ | 134 |
| 42 | 6-Cl | H | $CH_2C_6H_5$ | IPOC | 165 |
| 43 | 6-Cl | H | $C_2H_4SCH_3$ | $C_5H_9$ | Oil |
| 44 | 6-Cl | H | $C_2H_4SCH_3$ | IPOC | 135 |
| 45 | 6-Cl | H | $C_2H_4SOCH_3$ | IPOC | Oil |
| 46 | 6-Cl | H | $CH_2(OH)$ | $C_5H_9$ |  |
| 47 | 6-Cl | H | $CH_2CH(CH_3)_2$ | $C_5H_9$ | Oil |
| 48 | 6-Cl | H | $CH_2CH(CH_3)_2$ | ALOC | 140 |
| 49 | 6-Cl | H | $CH_2CH(CH_3)_2$ | IPOC | 148 |
| 50 | 6,7-$Cl_2$ | H | $CH_3$ | $C_5H_9$ |  |
| 51 | 8-Cl | H | $CH_3$ | $C_5H_9$ |  |
| 52 | 5-Cl | H | $CH_3$ | $C_5H_9$ | 150 decomp. |
| 53 | 7-Cl | H | $CH_3$ | $C_5H_9$ | Oil |
| 54 | 7-Cl | H | $CH_3$ | ALOC | 129 |
| 55 | 7-Cl | H | $CH_3$ | IPOC | 166 |
| 56 | 7-Cl | H | $CH(CH_3)_2$ | $C_5H_9$ | 221 |
| 57 | 7-Cl | H | $CH(CH_3)_2$ | IPOC | 151 |
| 58 | 7-Cl | H | $CH(CH_3)_2$ | ALOC | 142 |
| 59 | 7-Cl | H | $CH_2C_6H_5$ | $C_5H_9$ | Oil |
| 60 | 7-Cl | H | $CH_2C_6H_5$ | IPOC | 178 |
| 61 | 7-Cl | H | $C_2H_4SCH_3$ | $C_5H_9$ | 98 |
| 62 | 7-Cl | H | $C_2H_4SCH_3$ | IPOC | 148 |
| 63 | 7-Cl | H | $C_2H_4SCH_3$ | ALOC | 116 |
| 64 | 7-F | H | $CH_3$ | $C_5H_9$ | 75 |
| 65 | 7-F | H | $CH_3$ | ALOC | 155 |
| 66 | 7-F | H | $CH_3$ | IPOC | 168 |

TABLE 3-continued

| Nr. | $R^1_n$ | $R^2$ | $R^3$ | $R^5$ | M.P. °C. |
|---|---|---|---|---|---|
| 67 | 6-F | H | $CH_3$ | $C_5H_9$ | 153 |
| 68 | 6-F | H | $CH_3$ | ALOC | 120 |
| 69 | 6-F | H | $CH_3$ | IPOC | 175 |
| 70 | 7-$CF_3$ | H | $CH_3$ | $C_5H_9$ | 145 |
| 71 | 7-$CF_3$ | H | $CH_3$ | IPOC | 186 |
| 72 | 7-$C_6H_5O$ | H | $CH_3$ | $C_5H_9$ | 107 |
| 73 | 7-$C_6H_5O$ | H | $CH_3$ | IPOC | 172 |
| 74 | 6-Cl | H | $C_2H_4SO_2CH_3$ | IPOC | 160 decomp. |
| 75 | 6-Cl | H | $CH_2SCH_3$ | $C_5H_9$ | 118 |
| 76 | 6-Cl | H | $CH_2SCH_3$ | IPOC | 182 |
| 77 | 6-Cl | H | $CH_2SOCH_3$ | IPOC | 202 decomp. |
| 78 | 6-Cl | H | $CH_2SO_2CH_3$ | IPOC | 212 decomp. |
| 79 | 6-Cl | H | $CH(CH_3)CH_2CH_3$ | $C_5H_9$ | 87 |
| 80 | 6-Cl | H | $CH(CH_3)CH_2CH_3$ | ALOC | 74 |
| 81 | 6-Cl | H | $CH(CH_3)CH_2CH_3$ | IPOC | 142 |
| 82 | 6-F | H | $CH_3$ | $COCH_3$ | 186 |
| 83 | 6-Cl | H | $CH_3$ | $COCH_2OH$ | 185 |
| 84 | 6-Cl | H | $CH_3$ | 2-$COC_4H_3S$ | 112 |
| 85 | 6-Cl | H | $CH_3$ | $COCH_2C_6H_5$ | 80 |
| 86 | 6-Cl | H | $CH_3$ | $COCH_2Cl$ | 168 |
| 87 | 6-Cl | H | $CH_3$ | $CO(CH_2)_3CH_3$ | Oil |
| 88 | 6-Cl | H | $CH_3$ | $CO(CH_2)_2CH_3$ | 68 |
| 89 | 6-Cl | H | $CH_3$ | $COCH_2CH_3$ | 148 |
| 90 | 6-Cl | H | $CH_3$ | $COCH_3$ | 232 |
| 91 | 6-Cl | H | $C_2H_4OCOOC_2H_5$ | $COOC_2H_5$ | 139–140 |
| 92 | 6-Cl | $CH_2C{\equiv}CH$ | $CH_3$ | H | 152–154 |
| 93 | 6-Cl | 2-$CH_2C_5H_4N$ | $CH_3$ | H | 128–130 |
| 94 | 6-Cl | $CH_2Ph$ | $CH_3$ | H | 126–127 |
| 95 | 6-Cl | $C_2H_5CH(CH_3)_2$ | $CH_3$ | H | 70–72 |
| 96 | 6-Cl | $CH_3$ | $CH_3$ | $C_5H_9$ | Oil |
| 97 | 6-Cl | $CH_3$ | $CH_3$ | H | 115 |
| 98 | 6-Cl | $COOC(CH_3)_3$ | $CH_3$ | H | 82–83 |
| 99 | 7-Cl | $C_5H_9$ | $CH_3$ | $C_5H_9$ | Resin |
| 100 | 7-Cl | $C_5H_9$ | $CH_3$ | H | 108 |
| 101 | 7-$PhOSO_2$ | $C_5H_9$ | $CH_3$ | $C_5H_9$ | Oil |
| 102 | 7-$PhOSO_2$ | $C_5H_9$ | $CH_3$ | H | Oil |
| 103 | | $C_2H_4OCH_3$ | $CH_3$ | $C_2H_4OCH_3$ | Oil |
| 104 | 6-Cl | H | $CH_3$ | $SO_2C_4H_3S$ | 264 |
| 105 | 6-Cl | H | —$CH_2CH_2OCH_2$— | | 210 |
| 106 | 6-Cl | H | $CH_3$ | $COCH_2N(C_2H_5)_2$ | 108 |
| 107 | 6-Cl | H | $CH_3$ | $COCH_2N(CH_3)_2$ | 166 |
| 108 | 6-Cl | H | $CH_3$ | $COCH_2N(C_2H_4)_2O$ | 190 |
| 109 | 6-Cl | H | $CH_3$ | $COCH_2N(CH_2)_4$ | 185 |
| 110 | 6-Cl | H | $CH_3$ | $COCH_2N(CH_2)_5$ | 164 |
| 111 | 6-Cl | H | $CH_3$ | $COCH_2$—(4-methylpiperazin-1-yl) | 176 |
| 112 | 6-Cl | H | $CH_3$ | CO-4-$C_5H_4N$ | 214 |
| 113 | 6-Cl | H | $CH_3$ | $COCH_2NHCH_2CH{=}CH_2$ | 152 |
| 114 | 6-Cl | H | $CH_3$ | $COCH_2C_4H_3S$ | 155–156 |
| 115 | 6-Cl | H | $CH_2O$—t.-Bu | $C_5H_9$ | Oil |
| 116 | 6-Cl | H | $CH_2O$—t.-Bu | ALOC | Oil |
| 117 | 6-Cl | H | $CH_2O$—t.-Bu | IPOC | 154 |
| 118 | 6-Cl | H | $CH_2S$—i.-Pr | $C_5H_9$ | Oil |
| 119 | 6-Cl | H | $CH_2S$—i.-Pr | IPOC | 158 |
| 120 | 6-Cl | H | $CH_2S$—Bn | $C_5H_9$ | Oil |
| 121 | 6-Cl | H | $CH_2$—S—Bn | IPOC | Oil |
| 122 | 6,7-$Cl_2$ | H | $CH_3$ | $C_5H_9$ | 160 |
| 123 | 6,7-$Cl_2$ | H | $CH_3$ | IPOC | |
| 124 | 6-Cl | H | $C_4H_9$ | IPOC | 158 |
| 125 | 6-Cl | H | $C_4H_9$ | ALOC | 100 |
| 126 | 6-Cl | H | $CH_3$ | $(C_4H_3S)$-2-$CH_2CO$ | 156 |
| 127 | 6-Cl | H | $CH_2SCH_3$ | $COOCH(CH_3)_2$ | 157 |

TABLE 3-continued

[Structure: quinoxalin-2-one with R¹ₙ, R², R³, R⁵ substituents]

| Nr. | R¹ₙ | R² | R³ | R⁵ | M.P. ° C. |
|---|---|---|---|---|---|
| 128 | 6-CH$_3$O | H | CH$_2$SCH$_3$ | IPOC | 152 |
| 129 | 6-CH$_3$O | H | CH$_2$SCH$_3$ | COOCH(CH$_3$)$_2$ | 165 |

Key:
C$_5$H$_9$ = 3-methyl-2-buten-1-yl
C$_4$H$_7$ = 2-butenyl
C$_5$H$_{11}$ = 3-methyl-1-butyl
C$_6$H$_{11}$ = 2,2-dimethylcyclopropyl-1-methyl
sC$_6$H$_{11}$ = 4-methyl-3-penten-2-yl
C$_3$H$_3$ = 2-propen-1-yl
(CH$_3$)$_2$CCHCO = 3,3-dimethylacryl
IPOC = isopropenyloxycarbonyl
ALAC = allylaminocarbonyl
ALOC = allyloxycarbonyl
C$_4$H$_3$O = furanyl
C$_4$H$_3$S = thienyl
C$_5$H$_4$N = pyridyl
Ph = phenyl

EXAMPLE XVII

6,7-Dimethoxy-3-methyl-3,4-dihydroquinoxalin-2(1H)-one 4,5-Dimethoxy-1,2-dinitrobenzene (34.2 g, 0.15 mol) was hydrogenated in 500 ml of methanol with Raney nickel catalysis using 1 atm hydrogen. After the calculated amount of hydrogen had been taken up, the process was stopped, the catalyst was removed by filtration with suction, and the solvent was stripped off in vacuo. To remove the water completely, the mixture was taken up twice in methanol and reconcentrated. 4,5-Dimethoxy-1,2-phenylenediamine (24.0 g), which remained as a brown oil, was refluxed for 48 hours in 200 ml of ethanol (96%) together with 17.1 ml (0.15 mol) of methyl 2-chloropropionate, with an addition of 21.0 ml (0.15 mol) of triethylamine. The solution, which was very dark, was concentrated, the concentrate was taken up in ethyl acetate, the mixture was washed twice with water and dried (sodium sulfate), and the solvent was stripped off in vacuo. The crude product was crystallized by stirring with diethyl ether (6.2 g, 19%). A analytically pure sample of melting point 151° C. was obtained by silica gel chromatography using ethyl acetate as the eluent.

$^1$H NMR (60 MHz, d$_6$-DMSO): δ=1.22 (d, J=7 Hz, 3 H), 3.63 (s, 3 H), 3.67 (s, 1 H), 3.6–3.7 (m, 1 H), 5.62 (br. s, 1 H), 6.40 (s, 1 H), 6.45 (s, 1H), 9.90 ppm (br. s, 1 H). MS: M$^+$=222.

The following compounds of the formula I were synthesized in analogous manner and, if appropriate, derivatized further:

TABLE 4

[Structure: dihydroquinoxalin with R¹ₙ, R³, R⁵, X substituents]

| Nr. | R¹ₙ | R³ | R⁵ | X | M.P.° C. |
|---|---|---|---|---|---|
| 1 | 6,7-(CH$_3$O)$_2$ | CH$_3$ | IPOC | O | 133 |
| 2 | 6,7-(CH$_3$O)$_2$ | CH$_3$ | IPOC | S | |
| 3 | 6-C$_6$H$_5$S | CH$_3$ | C$_5$H$_9$ | O | 115 |
| 4 | 7-C$_6$H$_5$S | CH$_3$ | C$_5$H$_9$ | O | 107 |
| 5 | 6-C$_6$H$_5$S | CH$_3$ | H | O | |
| 6 | 7-C$_6$H$_5$S | CH$_3$ | H | O | |
| 7 | 6,7(CH$_3$O)$_2$ | CH$_3$ | H | O | 151 |

Key:
C$_5$H$_9$ = 3-methyl-2-buten-1-yl
IPOC = isopropenyloxycarbonyl

EXAMPLE XVIII

(3RS)-6-Chloro-4-N-(cyclopropyl)-3-methyl-3,4-dihydroquinoxalin-2(1H)-one

A) (2RS)-N-(4-Chloro-2-cyclopropylaminophenyl)-(2-bromopropionamide)

4-Chloro-2-cyclopropylaminonitrobenzene (2.10 g, 0.01 mol) was hydrogenated in 100 ml of methanol with Raney nickel catalysis, using 1 atm hydrogen. After the calculated amount of hydrogen had been taken up, the process was stopped, the catalyst was removed by filtration with suction, and the solvent was stripped off in vacuo. To remove water completely, the mixture was taken up twice in methanol and reconcentrated. 4-Chloro-2-cyclopropylaminoaniline (1.80 g), which remained in the form of a brown oil, was dissolved in 50 ml of anhydrous 1,2-dimethoxyethane and cooled to −60° C., with stirring. A solution of 1.1 ml (0.01 mol) of 2-bromopropionyl chloride in 5 ml of anhydrous 1,2-dimethoxyethane was slowly added dropwise, and stirring of the reaction mixture was continued for 2 hours at −60—−70° C. The mixture was then allowed to warm to approx. −20° C. and poured into 150 ml of ice-cold, saturated aqueous sodium hydrogen carbonate solution. The mixture was extracted twice using ethyl acetate, and the organic phase was washed once with water, dried (sodium sulfate) and concentrated in vacuo. After crystallization with diethyl ether/pentane, 2.51 g (79%) of the desired product of melting point 130° C. remained.

$^1$H NMR (270 MHz, $d_6$-DMSO): δ=0.4–0.5 (m, 2 H), 0.7–0.8 (m, 2 H), 1.75 (d, J=7 Hz, 3 H), 2.39 (m, 1 H), 4.72 (q, J=7 Hz, 1 H), 5.6 (br. s, 1 H), 6.66 (dd, J=8, 2 Hz, 1 H), 6.96 (d, J=2 Hz, 1 H), 7.21 (d, J=8 Hz, 1 H), 9.36 ppm (br. s, 1 H). MS: (M+H)$^+$=319, 317.

B) (3RS)-6-Chloro-4-N-(cyclopropyl)-3-methyl-3,4-dihydroquinoxalin-2(1H)-one

The compound of Example XVIIIA (318 mg, 1.0 mmol) was dissolved in 20 ml of ethanol (96%), 0.28 ml (2.0 mmol) of triethylamine were added, and the mixture was refluxed for 18 hours. The solvent was removed under reduced pressure, and the reaction product was purified by silica gel chromatography using ethyl acetate/heptane=1:2 as eluent. The yield was 200 mg (85%) of white crystals of melting point 167° C. (after crystallization from pentane).

$^1$H NMR (270 MHz, $d_6$-DMSO): δ=0.40 (m, 1 H), 0.63 (m, 1 H), 0.76 (m, 1 H), 0.98 (m, 1 H), 1.12 (d, J=7 Hz, 3 H), 2.47 (m, 1 H), 3.87 (q, J=7 Hz, 1 H), 6.78 (s, 2 H), 7.0 (s, 1 H), 10.46 ppm (br. s, 1 H). MS: (M+H)$^+$=237.

The following compounds of the formula I were synthesized analogously to the procedure described in Example XVIII using the correspondingly substituted orthonitroanilines and 2-halo carboxylic acid derivatives and, if appropriate, derivatized further:

TABLE 5

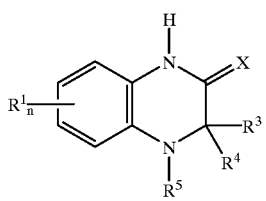

| Nr. | $R^1_n$ | $R^3$ | $R^4$ | $R^5$ | X | M.P.° C. |
|---|---|---|---|---|---|---|
| 1 | 6-Cl | CH$_3$ | H | C$_6$H$_5$ | O | 191 |
| 2 | 6-Cl | CH$_3$ | CH$_3$ | C$_3$H$_5$ | O | |
| 3 | 6-Cl | CH$_3$ | CH$_3$ | C$_3$H$_5$ | S | |
| 4 | 6-Cl | CH$_3$ | CH$_3$ | C$_3$H$_5$ | O | |
| 5 | 6-Cl | CH$_3$ | CH$_3$ | C$_3$H$_5$ | S | |

Key:
C$_3$H$_5$ = cyclopropyl
C$_6$H$_5$ = phenyl

EXAMPLE XIX

7-Chloro-1-N-(cyclopropyl)-3,3-dimethyl-3,4-dihydroquinoxalin-2(1H)-one

4-Chloro-2-cyclopropylaminonitrobenzene (2.0 g, 9.4 mmol) was hydrogenated as described in Example XVIIIA. The resulting 4-chloro-2-cyclopropylaminoaniline (1.70 g) was taken up in 20 ml of dichloromethane. 1.6 ml (2.01 mmol) of chloroform, 1.8 ml (2.45 mmol) of acetone and 0.10 g (0.4 mmol) of benzyltriethylammonium chloride were added, and the reaction solution was cooled to 10° C. 4 ml of 50% strength sodium hydroxide solution were slowly added dropwise with vigorous stirring, during which process the reaction temperature should not exceed 10° C. After stirring for 5 hours at 10° C., the phases were diluted and separated. The organic phase was washed once with water, dried (magnesium sulfate) and evaporated in vacuo. The crude product was purified by silica gel chromatography using ethyl acetate/heptane=1:2 as the eluent. The yield was 1.0 g (42%) of white crystals of melting point 132–133° C. (after recrystallization from toluene/heptane).

$^1$H NMR (270 MHz, $d_6$-DMSO): δ=0.45–0.55 (m, 2 H), 1.05–1.1 (m, 2 H), 1.19 (s, 6 H), 2.71 (m, 1 H), 6.09 (br. s, 1 H), 6.71 (d, J=8 Hz, 1 H), 6.88 (dd, J=8, 2 Hz, 1 H), 7.19 ppm (d, J=2 Hz, 1 H). MS: (M+H)$^+$=251.

The following compounds of the formula I were synthesized in analogous manner and, if appropriate, derivatized further:

TABLE 6

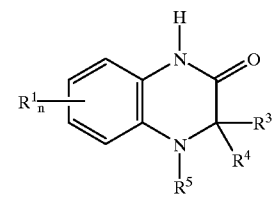

| Nr. | $R^1_n$ | $R^3$ | $R^4$ | $R^5$ | M.P.° C. |
|---|---|---|---|---|---|
| 1 | 6-Cl | CH$_3$ | CH$_3$ | C$_5$H$_9$ | 179 |
| 2 | 7-Cl | CH$_3$ | CH$_3$ | C$_5$H$_9$ | 171 |
| 3 | 6,7-(CH$_3$O)$_2$ | CH$_3$ | CH$_3$ | H | |
| 4 | 6,7-(CH$_3$O)$_2$ | CH$_3$ | CH$_3$ | C$_5$H$_9$ | |
| 5 | | CH$_3$ | CH$_3$ | sC$_6$H$_{11}$ | 113 |
| 6 | | C$_6$H$_5$ | CH$_3$ | H | |
| 7 | | C$_6$H$_5$ | CH$_3$ | C$_5$H$_9$ | |
| 8 | 6-Cl | CH$_3$ | CH$_3$ | IPOC | 128 |
| 9 | 7-Cl | CH$_3$ | CH$_3$ | IPOC | 169 |
| 10 | 7-CH$_3$ | CH$_3$ | CH$_3$ | C$_5$H$_9$ | 168 |
| 11 | 6-CH$_3$O | CH$_3$ | CH$_3$ | H | 200 |
| 12 | 6-CH$_3$O | CH$_3$ | CH$_3$ | C$_5$H$_9$ | 138 |
| 13 | 6/7-COOH | CH$_3$ | CH$_3$ | H | >240 |
| 14 | 6/7-COOH | CH$_3$ | CH$_3$ | C$_5$H$_9$ | 180 |
| 15 | 8-CH$_3$ | CH$_3$ | CH$_3$ | H | 140 |
| 16 | 8-CH$_3$ | CH$_3$ | CH$_3$ | C$_5$H$_9$ | 160 |
| 17 | 8-CH$_3$ | CH$_3$ | CH$_3$ | IPOC | 127 |
| 18 | 6/7-CH$_3$ | C$_2$H$_5$ | C$_2$H$_5$ | H | 160 |
| 19 | 6-CH$_3$ | C$_2$H$_5$ | C$_2$H$_5$ | C$_5$H$_9$ | 100 |
| 20 | 7-CH$_3$ | C$_2$H$_5$ | C$_2$H$_5$ | C$_5$H$_9$ | 110 |
| 21 | 7-F | CH$_3$ | CH$_3$ | H | 120 |
| 22 | 7-F | CH$_3$ | CH$_3$ | C$_5$H$_9$ | 155 |
| 23 | 7-C$_2$H$_5$O | CH$_3$ | CH$_3$ | H | 155 |
| 24 | 7-C$_2$H$_5$O | CH$_3$ | CH$_3$ | C$_5$H$_9$ | 123 |
| 25 | 6-COOH | CH$_3$ | CH$_3$ | C$_5$H$_9$ | 245 |
| 26 | 7,8-(CH$_3$)$_2$ | CH$_3$ | CH$_3$ | H | 196 |
| 27 | 7,8-(CH$_3$)$_2$ | CH$_3$ | CH$_3$ | C$_5$H$_9$ | 155 |
| 28 | 6,7-(CH$_3$)$_2$ | CH$_3$ | CH$_3$ | H | 248 |
| 29 | 6,7-(CH$_3$)$_2$ | CH$_3$ | CH$_3$ | C$_5$H$_9$ | 200 |
| 30 | 6-Cl,7-(2,3-Cl$_2$C$_6$H$_3$O) | CH$_3$ | CH$_3$ | H | 211 |
| 31 | 6-Cl,7-(2,3-Cl$_2$C$_6$H$_3$O) | CH$_3$ | CH$_3$ | C$_5$H$_9$ | 205 |
| 32 | 7-F | CH$_3$ | CH$_3$ | IPOC | 175 |
| 33 | 7-C$_2$H$_5$O | CH$_3$ | CH$_3$ | IPOC | 150 |
| 34 | 6/7-CH$_3$ | CH$_3$ | CH$_3$ | IPOC | 152 |
| 35 | 7,8-(CH$_3$)$_2$ | CH$_3$ | CH$_3$ | IPOC | 147 |
| 36 | 6,7-(CH$_3$)$_2$ | CH$_3$ | CH$_3$ | IPOC | 161 |
| 37 | 7-C$_6$H$_5$ | CH$_3$ | CH$_3$ | H | 167 |
| 38 | 7-C$_6$H$_5$O | CH$_3$ | CH$_3$ | C$_5$H$_9$ | 138 |
| 39 | 7-C$_6$H$_5$O | CH$_3$ | CH$_3$ | IPOC | 181 |
| 40 | 5-CH$_3$ | CH$_3$ | CH$_3$ | H | 182 |
| 41 | 6-CH$_3$O, | CH$_3$ | CH$_3$ | H | >240 |

TABLE 6-continued

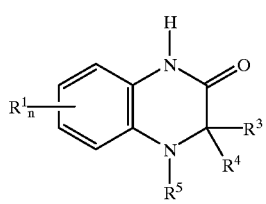

| Nr. | $R^1_n$ | $R^3$ | $R^4$ | $R^5$ | M.P.° C. |
|---|---|---|---|---|---|
| 42 | 7-(4-Pyridyl) 6-Cl, 7-Piperidino | CH₃ | CH₃ | H | 219 |
| 43 | 6/7-Cl,7/6-Morpholino (mixture) | CH₃ | CH₃ | H | 236 |
| 44 | 6/7-(N-Methyl-piperazin-1-yl) | CH₃ | CH₃ | H | >240 |
| 45 | 6/7-Cl,7/6-(N-Methyl-piperazin-1-yl) | CH₃ | CH₃ | H | 147 |
| 46 | 6-Cl | CH₃ | CH₃ | H | 152–154 |
| 47 | 7-Cl | CH₃ | CH₃ | H | |
| 48 | 6-Cl | CH₃ | CH₃ | ALOC | 128–129 |
| 49 | 7-Cl | CH₃ | CH₃ | ALOC | 144 |
| 50 | 6-Cl | CH₃ | CH₃ | COOCH(CH₃)₂ | 118 |
| 51 | 7-Cl | CH₃ | CH₃ | COOCH(CH₃)₂ | 171 |
| 52 | 7-(4-F—Ph—SO₂O) | CH₃ | CH₃ | H | |
| 53 | 7-(4-F—Ph—SO₂O) | CH₃ | CH₃ | IPOC | 204 |
| 54 | 6-Cl,7-Piperidino | CH₃ | CH₃ | IPOC | 152 |
| 55 | 6-Cl,7-Morpholino | CH₃ | CH₃ | IPOC | 113 |
| 56 | 6-Cl,7-(N-Methyl-piperazin-1-yl) | CH₃ | CH₃ | IPOC | 168 |
| 57 | 6-Cl,7-NEt₂ | CH₃ | CH₃ | H | 141 |
| 58 | 6-Cl,7-NEt₂ | CH₃ | CH₃ | IPOC | Oil |
| 59 | 6,7-Cl₂ | CH₃ | CH₃ | H | 232 |
| 60 | 6,7-Cl₂ | CH₃ | CH₃ | IPOC | 171 |
| 61 | 7-(N-Methyl-piperazinyl-1-yl) | CH₃ | CH₃ | H | 198 |
| 62 | 7-(N-Methyl-piperazinyl-1-yl) | CH₃ | CH₃ | IPOC | 123 |
| 63 | 6-CH₃O | CH₃ | CH₃ | IPOC | 128 |
| 64 | 7-Cl | —(CH₂)₃— | | IPOC | 172 |
| 65 | 7-Cl | —(CH₂)₄— | | IPOC | 181 |
| 66 | 6-Cl | —(CH₂)₃— | | IPOC | 157–158 |
| 67 | 6-Cl | —(CH₂)₄— | | IPOC | 179–180 |
| 68 | 6-Clq | CH₃ | CH₃ | COOC₂H₅ | 137 |
| 69 | 6-Cl | CH₃ | CH₃ | COOC₃H₇ | 125 |

Key:
C₅H₉ = 3-methyl-2-buten-1-yl
sC₆H₁₁ = 4-methyl-3-penten-2-yl
IPOC = isopropenyloxycarbonyl

EXAMPLE XX 3,3-Dimethyl-4-N-(3-methyl-2-buten-1-yl)-3,4-dihydroquinoxalin-2(1H)-one The compound was prepared analogously to the compound described in Example VIA, starting from 3,3-dimethyl-3,4-dihydroquinoxalin-2(1H)-one (J. T. Lai, Synthesis 1982, 71). Melting point 146–147° C. (after crystallization from methyl tert.-butyl ether/heptane).

¹H NMR (270 MHz, d₆-DMSO): δ=1.27 (s, 3 H), 1.68 (s, 3 H), 1.72 (s, 3 H), 3.88 (d, J=7 Hz, 1 H), 5.15 (m, 1 H), 6.60 (d, J=7 Hz, 1 H), 6.67 (t, J=7 Hz, 1 H), 6.78 (d, J=7 Hz, 1 H), 6.87 (t, J=7 Hz, 1 H), 10.33 ppm (br. s, 1 H). MS: (M+H)⁺=245.

EXAMPLE XXI

4-N-(3-Methyl-2-buten-1-yl)-3,4-dihydroquinoxalin-2(1H)-one-3-spiro-1'-cyclohexane The compound was prepared analogously to the compound described in Example VIA, starting from spiro[cyclohexane-1,3'-(3',4'-dihydroquinoxalin-(1'H)-one)] (J. T. Lai, Synthesis 1982, 71). Melting point 82–83° C. (after crystallization from heptane).

¹H NMR (270 MHz, d₆-DMSO): δ=1.25–1.75 (m, 10 H), 3.75 (d, J=6 Hz, 2 H), 5.07 (m, 1 H), 6.7–7.0 (m, 4 H), 10.15 ppm (br. s, 1 H). MS: (M+H)⁺=285.

EXAMPLE XXII

4-N-(3-Methyl-2-buten-1-yl)-3,4-dihydroquinoxaline-2(1H)-thione-3-spiro-1'-cyclohexane The compound of Example XXI (500 mg, 1.8 mmol) was refluxed for 1.5 hours under argon together with 370 mg (0.9 mmol) of 2,4-bis-(4-methoxyphenyl)-1,3-dithia-2,4-diphosphetane 2,4-disulfide (Lawesson's reagent) in 10 ml of anhydrous toluene. The mixture was subsequently concentrated in vacuo, and the products were isolated by silica gel chromatography using methyl tert.-butyl ether/heptane= 10:1 as eluent. The yield was 50 mg (9%) of yellow crystals of melting point 125° C.

¹H NMR (270 MHz, d₆-DMSO): δ=1.1–1.9 (m, 16 H), 3.64 (d, J=7 Hz, 2 H), 4.99 (m, 1 H), 6.95–7.1 (m, 3 H), 7.18 (d, J=7 Hz, 1 H), 12.2 ppm (br. s, 1 H). MS: (M+H)⁺=301.

3,4-Dihydroquinoxaline-2(1H)-thione-3-spiro-1'-cyclohexane was isolated as a further product in a yield of 110 mg (26%); yellow crystals of melting point 178° C.

¹H NMR (270 MHz, $_c$DCl₃ δ=1.25–2.2 (m, 10 H), 4.18 (br. s, 1 H), 6.7–6.8 (m, 3 H), 6.97 (m, 1 H), 9.42 ppm (br. s, 1 H). MS: (M+H)⁺=233.

EXAMPLE XXIII (3S)-6-Chloro-4-N-(isopropenyloxycarbonyl)-3-methyl-3,4-dihydroquinoxaline-2(1H)-thione The compound of Example XIII (0.5 g, 1.78 mmol), dissolved in 10 ml of anhydrous pyridine, was refluxed for 4 hours together with 0.47 g (2.12 mmol) of phosphorus pentasulfide. The mixture was concentrated in vacuo, and the residue was chromatographed on silica gel using ethyl acetate/heptane=1:1 as eluent. This gave 0.25 g (47%) of a yellow crystalline solid of melting point 148–150° C. (after recrystallization from ethyl acetate/heptane).

¹H NMR (270 MHz, d₆-DMSO): δ=1.24 (d, J=7 Hz, 3 H), 1.96 (s, 3 H), 4.8–4.9 (m, 2 H), 5.28 (q, J=7 Hz, 1 H), 7.22 (d, J=8 Hz, 1 H), 7.30 (dd, J=8, 2 Hz, 1 H), 7.72 (br. s, 1 H), 12.84 ppm (br. s, 1 H). MS: (M+H)⁺=297.

The following compounds of the formula I were synthesized in analogous manner from the corresponding 3,4-dihydroquinoxalin-2(1H)-ones:

TABLE 7

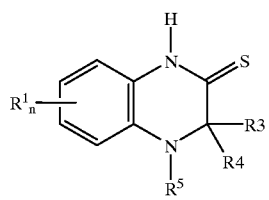

| Nr. | $R^1_n$ | $R^3$ | $R^4$ | $R^5$ | M.P. °C. |
|---|---|---|---|---|---|
| 1 |  | CH₃ | H | C₅H₉ | 119 |
| 2 | 6-Cl | CH₃ | H | C₅H₉ | 109–110 |
| 3 | 6-Cl | CH₃ | H | C₆H₅CH₂ | 92 |
| 4 | 6-Cl | H |  | —CH₂CH₂CS— |  |
| 5 | 6-Cl | H |  | —CH₂CH₂CH₂CS— |  |
| 6 |  | C₆H₅ | CH₃ | C₅H₉ |  |
| 7 | 6-Cl | CH₃ | CH₃ | C₅H₉ | 157 |
| 8 | 7-Cl | CH₃ | CH₃ | C₅H₉ | 160 |
| 9 | 7-Cl | CH₃ | CH₃ | H | 170 |
| 10 | 6-Cl | CH₃ | H | ALOC | 143–145 |
| 11 | 6-Cl | CH₃ | CH₃ | IPOC | 153 |
| 12 | 7-Cl | CH₃ | CH₃ | IPOC | 174 |
| 13 | 6-Cl | CH₃ | CH₃ | H | 175 |
| 14 | 6-Cl | C₂H₅ | H | IPOC | 176–177 |
| 15 | 6-Cl | C₂H₅ | H | ALOC | 159–161 |
| 16 | 6,7-(CH₃)₂ | CH₃ | CH₃ | C₅H₉ | 173 |
| 17 | 6-Cl | C₃H₇ | H | IPOC | 154–155 |
| 18 | 6-Cl | C₃H₇ | H | ALOC | 98–100 |
| 19 | 6-Cl | CH₃ | H | (2-C₅H₄N)—CH₂ | 175–178 |
| 20 | 6-Cl | CH₃ | H | (3-C₅H₄N)—CH₂ | 77 |
| 21 | 6-Cl | CH₃ | CH₃ | ALOC | 153–154 |
| 22 | 6-Cl | CH₃ | CH₃ | COOCH(CH₃)₂ | 151 |
| 23 | 6-Cl | CH₂SCH₃ | H | IPOC | 128 |
| 24 | 6-Cl | CH₃ | CH₃ | COOC₂H₅ | 163 |
| 25 | 6-Cl | CH₃ | CH₃ | COOC₃H₇ | 164 |
| 26 | 6-Cl | C₂H₅ | H | (2-C₅H₄N)—CH₂ | 162–164 |
| 27 | 6-Cl | C₄H₉ | H | IPOC | 132 |
| 28 | 6-Cl | CH₂SCH₃ | H | COOCH(CH₃)₂ | 124 |
| 29 | 6-Cl | CH₂SCH₃ | J | (2-C₅H₄N)—CH₂ | 159 |
| 30 | 6-CH₃O | CH₂SCH₃ | H | IPOC | 154 |
| 31 | 6-CH₃O | CH₂SCH₃ | H | COOCH(CH₃)₂ | 163 |
| 32 | 6-Cl | CH₂SCH₃ | H | CH₂C₆H₄-2-Cl | Oil |

Key:
C₅H₉ = 3-methyl-2-buten-1-yl
IPOC = isopropenyloxycarbonyl
ALOC = allyloxycarbonyl
C₅H₄N = pyridyl

EXAMPLE XXIV (3RS)-3-Methyl-4-N-(3-methyl-2-buten-1-yl)-2-methylthio-3,4-dihydroquinoxaline (3RS)-3-Methyl-4-N-(3-methyl-2-buten-1-yl)-3,4-dihydroquinoxaline-2(1H)-thione (Table 7, No. 1) (0.49 g, 2.0 mmol) was dissolved in 20 ml of ethanol (96%), and the solution was treated with 5.1 ml (2.2 mmol) of a 1% strength sodium ethanolate solution. After the mixture had been stirred for 15 minutes at room temperature, 0.14 ml (2.2 mmol) of methyl iodide was added dropwise, and the mixture was stirred for a further 2 hours at room temperature. The reaction solution was concentrated, and the residue was chromatographed on silica gel. 500 mg (96%) of a yellow oil were isolated using ethyl acetate/heptane=1:6.

$^1$H NMR d₆-DMSO): δ=0.96 (d, J=7 Hz, 3 H), 1.72 (s, 6 H), 2.44 (s, 3 H), 3.71 (dd, J=15, 6 Hz, 1 H), 3.89 (dd, J=15, 6 Hz, 1 H), 4.00 (q, J=7 Hz, 1 H), 5.20 (m, 1 H), 6.65–6.75 (m, 2 H), 7.02 (t, J=8 Hz, 1 H), 7.11 ppm (d, J=8 Hz, 1 H). MS: (M+H)⁺=261.

The following compound of the formula I was synthesized in the same manner:

4-Isopropenyloxycarbonyl-2-(isopropenyloxycarbonyl)-thio-3,3,7,8-tetramethyl-3,4-dihydroquinoxaline.

Melting point: 115° C.

EXAMPLE XXV (3RS)-3-Methyl-4-N-(3-methyl-2-buten-1-yl)-3,4-dihydroquinoxalin-2(1H)-one (3RS)-3-Methyl-3,4-dihydroquinoxalin-2(1H)-one (4.86 g, 0.03 mol) dissolved in 50 ml of N,N-dimethylformamide, was alkylated with 4.2 ml (0.033 mol) of 3-methyl-2-buten-1-yl bromide (90%) in the presence of 4.60 g (0.033 mol) of pulverulent potassium carbonate. The reaction mixture was stirred at room temperature until reaction of the educt was complete. The solvent was then stripped off in vacuo, the residue was taken up in ethyl acetate and water, the phases were separated, the aqueous phase was extracted twice with ethyl acetate, and the combined organic extracts were washed twice with water. Drying over sodium sulfate, concentration in vacuo and crystallization from pentane gave 5.80 g (84%) of white crystalline product of melting point 92–93° C.

$^1$H NMR (270 MHz, d$_6$-DMSO): δ=0.99 (d, J=7 Hz, 3 H), 1.72 (s, 6 H), 3.67 (dd, J=15, 7 Hz, 1 H), 3.86 (q, J=7 Hz, 1 H), 3.88 (dd, J=15, 7 Hz, 1 H), 5.21 (m, 1 H), 6.65–6.9 (m, 4 H), 10.31 ppm (br. s, 1 H). MS: (M+H)$^+$=231.

EXAMPLE XXVI 3,3a-Dihydropyrrolo[1,2-a]quinoxaline-1,4(2H,5H)-dione

2-Fluoronitrobenzene (14.1 g, 0.1 mol) and L-glutamic acid (45.0 g, 0.3 mol) were heated in 100 ml of 2-methoxyethanol at 95° C., with stirring, and 300 ml of 2N sodium hydroxide solution were added dropwise. Stirring was then continued for another 3 hours at this temperature. After cooling, the solution was treated with 400 ml of methanol and hydrogenated under atmospheric pressure with Raney nickel as catalyst.

When the uptake of hydrogen had ended, the catalyst was removed by filtration with suction, and the solution was concentrated under reduced pressure. The residue was acidified with 250 ml of 2N hydrochloric acid and heated in a steam bath for approx. 30 minutes. The precipitate which resulted in this process was filtered off with suction, washed with water and alcohol and subsequently dried, melting point 255° C., decomposition.

$^1$H NMR (60 MHz, d$_6$-DMSO): δ=1.9–2.7 (m, 4 H), 4.5 (t, J=8 Hz, 1 H), 6.8–7.3 (m, 3 H), 7.8–8.2 (m, 1 H), 10.7 ppm (br. s, 1 H). MS: (M+H)$^+$=202.

EXAMPLE XXVII

7-Phenoxysulfonyl-3,3a-dihydropyrrolo[1,2-a]quinoxaline-1,4(2H,5H)-dione

The compound was obtained in analogous manner by reacting phenyl 4-chloro-3-nitrobenzenesulfonate with L-glutamic acid, melting point 140° C. (decomp.).

$^1$H NMR (60 MHz, d$_6$-DMSO): δ=1.6–2.5 (m, 4 H), 4.07 (t, J=6 Hz, 1 H), 6.7–7.6 (m, 8 H), 10.57 ppm (br. s, 1 H). MS: (M+H)$^+$=358.

EXAMPLE XXVIII

3-Carboxymethyl-3,4-dihydroquinoxalin-2(1H)-one

2-Fluoronitrobenzene (14.1 g, 0.1 mol) and L-aspartic acid (40.0 g, 0.3 mol) were heated to 95° C. in 100 ml of 2-methoxyethanol, with stirring, and 300 ml of 2N sodium hydroxide solution were added dropwise. Stirring was then continued for 1 hour at this temperature. After the solution had cooled, it was treated with 500 ml of methanol and hydrogenated under atmospheric pressure with Raney nickel as catalyst.

When the uptake of hydrogen had ended, the catalyst was removed by filtration with suction, and the solution was concentrated under reduced pressure. The residue was acidified with 500 ml of 2N hydrochloric acid, the mixture was subsequently concentrated, neutralized with sodium acetate and extracted with ethyl acetate. The mixture was dried with sodium sulfate, the solvent was stripped off, and the residue was then obtained which was first oily and crystallized upon stirring with water, melting point 152–154° C.

$^1$H NMR (60 MHz, d$_6$-DMSO): δ=2.5–2.7 (dd partly concealed, 2 H), 4.1 (td, J=6, 2 Hz, 1 H), 5.98 (br. s, 1 H), 6.5–6.9 (m, 4 H), 10.30 (br. s, 1 H), 12.37 ppm (br. s, 1 H). MS: M+=206; CHN analysis: calculated C, 58.2; H, 4.8; N 13.6%; found C, 58.4; H, 4.7; N, 13.7%.

EXAMPLE XXIX

7-Phenoxysulfonyl-3,4-dihydroquinoxalin-2(1H)-one

A) Methyl N-[(2-nitro-4-phenoxysulfonyl)phenyl]glycinate

Phenyl 4-chloro-3-nitrobenzenesulfonate (62.7 g, 0.2 mol) and methyl glycinate hydrochloride (100.4 g, 0.8 mol), dissolved in 250 ml of methanol, were treated with 200 ml of triethylamine, and the mixture was refluxed for 15 minutes. After cooling, the mixture was treated with 1 l of 2N acetic acid, subjected to filtration with suction and washed with water. The residue was recrystallized from ethyl acetate and washed with methanol and diisopropyl ether, melting point 120–123° C.

B) 7-Phenoxysulfonyl-3,4-dihydroquinoxalin-2(1H)-one

Methyl N-[(2-nitro-4-phenoxysulfonyl)phenyl]glycinate (36.6 g, 0.1 mol) was hydrogenated under atmospheric pressure in a mixture of 250 ml of N,N-dimethylformamide and 250 ml of methanol, with Raney nickel as catalyst. When the uptake of hydrogen had ended, the catalyst was removed by filtration with suction, and the solution was freed from solvent in vacuo. The residue was dissolved in 40 ml of 2-methoxyethanol, and the mixture was heated for one hour in a steam bath. The resulting precipitate was filtered off with suction and washed with methanol, melting point 253–254° C.

$^1$H NMR (60 MHz, d$_6$-DMSO): δ=4.0 (d, J=4 Hz, 2 H), 6.6–7.6 (m, 9 H), 10.43 ppm (br. s, 1 H). MS: (M+H)$^+$=305.

EXAMPLE XXX 4-(3-Methyl-2-buten-1-yl)-7-phenoxysulfonyl-3,4-dihydroquinoxalin-2(1H)-one 7-Phenoxysulfonyl-3,4-dihydroquinoxalin-2(1H)-one (1.52 g, 5.0 mmol) in 20 ml of N,N-dimethylacetamide was stirred for 8 hours at 100° C. with 2 ml of 3-methyl-2-buten-1-yl bromide. After cooling, the mixture was treated with water and extracted with ethyl acetate. The solution was dried using magnesium sulfate and then concentrated, and the residue was chromatographed over a silica gel column using ethyl acetate/heptane=1:1. The fractions which contained the substance were evaporated on a rotary evaporator, and the product was subsequently stirred with pentane and filtered off with suction, melting point 132° C.

$^1$H NMR (270 MHz, d$_6$-DMSO): δ=1.73 (s, 6 H), 3.90 (s, 2 H), 3.93 (partly concealed d, J=6 Hz, 2 H), 5.20 (br. t, J=6 Hz, 1 H), 6.75–7.45 (m, 8 H), 10.66 ppm (s, 1 H). MS: (M+H)$^+$=373.

The following compounds of the formula I were synthesized in analogous manner using the corresponding haloaromatic substances and amino acid derivatives and, if appropriate, derivatized further on nitrogen atom 4:

TABLE 8

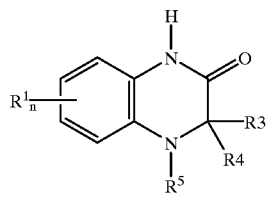

| Nr. | R¹ₙ | R³ | R⁴ | R⁵ | M.P. °C. |
|---|---|---|---|---|---|
| 1 | 7-C₆H₅—O—SO₂ | H | CH₂OH | H | 199 |
| 2 | 7-C₆H₅—O—SO₂ | H | CH₂OH | C₅H₉ | 120 |
| 3 | 7-C₆H₅—O—SO₂ | H | CH₂COOH | H | 230 decomp. |
| 4 | 7-C₆H₅—O—SO₂ | H | CH₂COOH | C₅H₉ | |
| 5 | 7-C₆H₅—O—SO₂ | H | CH₂CONH₂ | H | 272 decomp. |
| 6 | 7-C₆H₅—O—SO₂ | H | CH₂CONH₂ | C₅H₉ | |
| 7 | 7-C₆H₅—O—SO₂ | H | CH₂-4-Imi | H | 216 decomp. |
| 8 | 7-C₆H₅—O—SO₂ | H | CH₂-4-Imi | C₅H₉ | |
| 9 | 7-C₆H₅—CO | H | H | H | 280 decomp. |
| 10 | 7-C₆H₅—CO | H | H | C₆H₅—CO | 277 decomp. |
| 11 | 7-C₆H₅—O—SO₂ | H | CH₃ | H | 148 |
| 12 | 7-C₆H₅—O—SO₂ | H | CH₃ | C₅H₉ | Oil |
| 13 | 7-C₆H₅—SO₂ | H | CH₃ | H | 198 |
| 14 | 7-C₆H₅—SO₂ | H | CH₃ | C₅H₉ | Oil |
| 15 | 7-C₆H₅—SO₂ | H | CH₃ | IPOC | 108 |
| 16 | 7-C₆H₅O—SO₂ | H | H | H | |
| 17 | 7-C₆H₅SO₂ | H | H | COCH₃ | 270 |
| 18 | 7-C₆H₅OSO₂ | H | CH₃ | IPOC | Resin |

Key:
C₅H₉ = 3-methyl-2-buten-1-yl
4-Imi = 4-imidazolyl
IPOC = isopropenyloxycarbonyl

EXAMPLE XXXI

6-Chloro-7-phenoxysulfonyl-1,2,3,3a-tetrahydropyrrolo[2,1-c]-quinoxalin-4(5H)-one A) Phenyl 2,4-dichloro-3-nitrobenzenesulfonate 2,6-Dichloronitrobenzene was stirred for 7 hours at 130° C. with an excess of chlorosulfonic acid. After cooling, the mixture was poured onto ice, the sulfochloride was filtered off with suction, washed to neutrality and dried over sodium hydroxide, melting point 91° C. The resulting sulfochloride (29.05 g, 0.1 mol) and phenol (11.5 g, 0.12 mol) were dissolved in 150 ml of acetone and treated with 14 ml of triethylamine at 10° C. The mixture was stirred for 1 hour with cooling, stirring was then continued for a further 4 hours at room temperature, the mixture was then treated with 200 ml of water, the resulting precipitate was filtered off with suction at 10° C., washed with water and dried in vacuo at 80° C., melting point 102° C.

B) N-[(3-Chloro-2-nitro-4-phenoxysulfonyl)phenyl]proline

Phenyl 2,4-dichloro-3-nitrobenzenesulfonate 34.8 g, 0.1 mol), 69.0 g (0.6 mol) of L-proline, 200 ml of 2N sodium hydroxide solution and 200 ml of 2-methoxyethanol were stirred for 10 minutes at 80° C. The clear solution was acidified at 50° C. using concentrated hydrochloric acid and poured onto ice. The precipitate was filtered off with suction, washed with water to neutrality and dried at 80° C. Melting point 148° C. (after recrystallization from methanol).

C) 6-Chloro-7-phenoxysulfonyl-1,2,3,3a-tetrahydropyrrolo[2,1-c]-quinoxalin-4(5H)-one N-[(3-Chloro-2-nitro-4-phenoxysulfonyl)phenyl]proline (38.0 g, 0.075 mol) in 500 ml of methanol and 25 ml of concentrated ammonia solution was hydrogenated under atmospheric pressure with Raney nickel as catalyst.

When the uptake of hydrogen had ended, the catalyst was removed by filtration with suction, the solution was concentrated, the residue together with 2N hydrochloric acid was heated for approximately 30 minutes in a steam bath, cooled, subjected to filtration with suction and washed with water to neutrality. Melting point 197° C. (after recrystallization from glacial acetic acid).

EXAMPLE XXXII 8-(4-Methyl-1-piperazinyl)-3-(2-methylpropyl)-5-phenoxysulfonyl-3,4-dihydroquinoxalin-2(1H)-one A) Phenyl 2-chloro-4-(4-methyl-1-piperazinyl)-3-nitrobenzenesulfonate Phenyl 2,4-dichloro-3-nitrobenzenesulfonate (17.4 g, 0.05 mol) and 25 ml of methylpiperazine in 100 ml of isopropanol were refluxed for 10 minutes and subsequently concentrated. The residue was stirred with 50 ml of 50% methanol, filtered off with suction, and washed with 50% methanol and finally with water. Melting point 94–95° C. (after recrystallization from cyclohexane).

B) N-[(3-(4-Methyl-1-piperazinyl)-2-nitro-6-phenoxysulfonyl)-phenyl]leucine hydrochloride Phenyl 2-chloro-4-(4-methyl-1-piperazinyl)-3-nitrobenzenesulfonate (41.1 g, 0.1 mol) and L-leucine (39.3 g, 0.3 mol) were stirred for 8 hours at 95° C. in a mixture of 100 ml of N,N-dimethylformamide, 50 ml of 2-methoxyethanol and 100 ml of 2N sodium hydroxide solution. When cold, the reaction mixture was acidified with concentrated hydrochloric acid. The precipitate was taken up in ethyl acetate, and the mixture was dried using sodium sulfate and freed from solvent in vacuo. This gave an orange oil.

C) 8-(4-Methyl-1-piperazinyl)-3-(2-methylpropyl)-5-phenoxysulfonyl-3,4-dihydroquinoxalin-2(1H)-one hydrochloride N-[(3-(4-Methyl-1-piperazinyl)-2-nitro-6-phenoxysulfonyl)-phenyl]leucine hydrochloride (25.3 g, 0.05 mol) in 250 ml of methanol and 25 ml of glacial acetic acid was hydrogenated under atmospheric pressure using Raney nickel as catalyst. When the uptake of hydrogen had ended, the catalyst was removed by filtration with suction, the solution was concentrated, and the residue together with 2N of hydrochloric acid was heated for approximately 10 minutes in a steam bath and then concentrated in vacuo. The residue was dissolved in water, the mixture was rendered alkaline using ammonia, and this was taken up in ethyl acetate. The oil which remained after concentration was dissolved in 400 ml of diisopropyl ether, and the mixture was rendered neutral using ethanolic hydrochloric acid. The precipitate was filtered off with suction, washed with diisopropyl ether and dried, melting point 90° C. and above (decomp.).

MS: M+=458.

The following compounds of the formula I were synthesized in analogous manner using the corresponding haloaromatic substances and amino acid derivatives and, if appropriate, derivatized further on nitrogen atom 4:

TABLE 9

| Nr. | $R^3$ | $R^4$ | $R^5$ | M.P. ° C. |
|---|---|---|---|---|
| 1 | H | $(CH_3)_2CHCH_2$ | $C_5H_9$ | |
| 2 | H | $CH_3$ | H | 100 decomp. (HCl) |
| 3 | H | $CH_3$ | $C_5H_9$ | |
| 4 | H | H | H | 126–127 (base) |
| 5 | H | H | $C_5H_9$ | |

Key:
$C_5H_9$ = 3-methyl-2-buten-1-yl

EXAMPLE XXXIII (3RS)-4-N-Cyclohexyl-3-methyl-3,4-dihydroquinoxalin-2(H)-one (3RS)-3-Methyl-3,4-dihydroquinoxalin-2(1H)-one (0.81 g, 0.005 mol) and 1 ml (0.1 mol) of cyclohexanone were introduced into 20 ml of 1,2-dichloroethane. Trifluoroacetic acid (1.9 ml, 0.025 mol) was added dropwise, during which process a clear solution formed with gentle heating. 2.1 g (0.01 mol) of sodium triacetoxyborohydride were added, the exothermic reaction was then allowed to $^1$H NMR (270 MHz, $d_6$-DMSO): δ=1.25 (d, J=7 Hz, 3 H), 3.83 (q, J=7 Hz, 1 H), 6.61 (dd, J=6, 2 Hz, 1 H), 6.70 (s, 2H), 10.3 ppm (br. s, 1 H). MS: (M+H)$^+$=259.

EXAMPLE XXXVI (3S)-6-Chloro-4-N-(2-methoxyethoxycarbonyl)-3-methyl-3,4-dihydroquinoxalin-2(1H)-one To a solution of 0.24 ml (3.0 mmol) of 2-methoxyethanol in 10 ml of anhydrous 1,2-dimethoxyethane there was added 0.16 g of a 55% suspension of sodium hydride in mineral oil, and the reaction mixture was stirred for 30 minutes at room temperature. 0.50 g (1.9 mmol) of the compound of Example XXXV was subsequently added, with ice-cooling, and the mixture was allowed to warm to room temperature and stirred for a further 30 minutes. The mixture was treated with saturated aqueous sodium chloride solution, extracted several times with ethyl acetate, the organic phase was washed once with saturated aqueous sodium chloride solution and dried (magnesium sulfate), and the solvent was removed in vacuo. After silica gel chromatography (ethyl acetate/heptane=1:1) and crystallization from ether/heptane, 0.29 g (51%) of the desired product was obtained, melting point 93–94° C.

$^1$H NMR (200 MHz, $d_6$-DMSO): δ=1.13 (d, J=7.5 Hz, 3 H), 3.32 (s, 3 H), 3.6 (m, 2H), 4.24 (m, 1 H), 4.35 (m, 1 H), 4.81 (q, J=7.5 Hz, 1 H), 6.98 (d, J=9 Hz, 1 H), 7.2 (dd, J=9, 3 Hz, 1 H), 7.66 (d, J=3 Hz, 1 H), 10.81 ppm (br. 2, 1 H). MS: (M+H)$^+$=299.

EXAMPLE XXXVII (3S)-6-Chloro-3-methyl-4-N-[(phenylthio)carbonyl)]-3,4-dihydroquinoxalin-2(1H)-one To a solution of 0.31 ml (3.0 mmol) of thiophenol in 10 ml of 1,2-dimethoxyethane there was added 0.17 g of a 55% suspension of sodium hydride in mineral oil, with proceed for 30 minutes with stirring, and quenching was then effected by adding saturated aqueous sodium hydrogen carbonate solution. The phases were separated, the organic phase was washed with saturated aqueous sodium chloride solution, dried (magnesium sulfate) and concentrated. The crude product was chromatographed on silica gel using ethyl acetate/heptane=1:1. 1.15 g (94%) of the desired product were obtained, melting point 131–132° C. (toluene/heptane).

$^1$H NMR (270 MHz, $d_6$-DMSO): δ=0.97 (d, J=7 Hz, 3 H), 1.0–2.0 (m, 10 H), 3.39 (m, 1 H), 3.91 (q, J=7 Hz, 1 H), 6.68–6.94 (m, 4 H), 10.27 ppm (br. s, 1 H). MS: (M+H)$^+$= 245.

The following compounds of the formula I were synthesized in analogous manner.

TABLE 10

| Nr. | $R^1_n$ | $R^3$ | $R^4$ | $R^5$ | M.P. ° C. |
|---|---|---|---|---|---|
| 1 | | $CH_3$ | H | $C_2H_5$ | 106–107 |
| 2 | | $CH_3$ | H | $CH_2C(CH_3)_3$ | 162 |
| 3 | | $CH_3$ | H | c-$C_5H_9$ | 120 |
| 4 | 6-Cl | $CH_3$ | H | c-$C_4H_7$ | 100 |
| 5 | 6-Cl | $CH_3$ | H | $C_5H_{11}$ | 94–95 |
| 6 | 6-Cl | $CH_3$ | H | $CH_2C(CH_3)_3$ | 158–160 |
| 7 | 6-Cl | $C_2H_5$ | H | $CH_2C(CH_3)_3$ | 158–159 |
| 8 | 6-Cl | $CH_3$ | H | CH=CHCHO | 140–146 |
| 9 | 6-Cl | $CH_3$ | H | $CH_2C\equiv CH_3$ | 166–168 |
| 10 | 6-Cl | $CH_3$ | H | 2-Picolyl | 198–199 |
| 11 | 6-Cl | $CH_3$ | H | 3-Picolyl | 136 |
| 12 | 6-Cl | $CH_3$ | H | 4-Picolyl | 191–193 |

TABLE 10-continued

| Nr. | R¹ₙ | R³ | R⁴ | R⁵ | M.P. ° C. |
|---|---|---|---|---|---|
| 13 | 6-Cl | $CH_3$ | H | Furanyl-2-methyl | 116–118 |
| 14 | 6-Cl | $CH_3$ | H | $CH_2C_6H_4$-4-Br | 149–150 |
| 15 | 6-Cl | $CH_3$ | H | $CH_2C_6H_4$-4-CN | 95–96 |
| 16 | 6-Cl | $CH_3$ | H | $CH_2C_6H_4$-4-$NO_2$ | 117 |
| 17 | 6-Cl | $CH_3$ | H | $CH_2C_6H_4$-3-$NO_2$ | 125 |
| 18 | 6-Cl | $CH_3$ | H | $CH_2C_6H_4$-2-$NO_2$ | 153–154 |
| 19 | 6-Cl | $CH_3$ | H | $CH_2C_6H_4$-4-Cl | 122–123 |
| 20 | 6-Cl | $CH_3$ | H | $CH_2C_6H_4$-3-Cl | 156–157 |
| 21 | 6-Cl | $CH_3$ | H | $CH_2C_6H_4$-2-Cl | 138 |
| 22 | 6-Cl | $CH_3$ | H | $CH_2C_6H_4$-4-F | 147 |
| 23 | 6-Cl | $CH_3$ | H | $CH_2C_6H_4$-4-$C_6H_5$ | 164–165 |
| 24 | 6-Cl | $CH_3$ | H | $CH_2C_6H_4$-4-$OC_6H_5$ | Oil |
| 25 | 6-Cl | $CH_3$ | H | $CH_2C_6H_4$-4-$CH_3$ | 60–62 |
| 26 | 6-Cl | $CH_3$ | H | $CH_2C_6H_4$-4-$COOCH_3$ | 139 |
| 27 | 6-Cl | $CH_3$ | H | $CH_2C_6H_3$-2,6-$Cl_2$ | 190–191 |
| 28 | 6-Cl | $CH_3$ | H | $CH_2C_6H_3$-3,5-$Cl_2$ | 139–140 |
| 29 | 6-Cl | $CH_3$ | H | Naphthyl-1-methyl | 164–166 |
| 30 | 6-Cl | $CH_3$ | H | Naphthyl-2-methyl | 161–164 |
| 31 | 6-Cl | $CH_3$ | H | $CH_2CH_2OCH_3$ | 78–79 |
| 32 | 6-Cl | $CH_3$ | H | Cyclohex-2-enyl | Oil |
| 33 | 6-Cl | $CH_3$ | H | $C_2H_4$—$C_6H_5$ | 128 |
| 34 | 6-Cl | $CH_3$ | H | Thienyl-3-methyl | 141–142 |
| 35 | 6-Cl | $CH_3$ | H | (5-Methylthienyl)-2-methyl | 58–60 |
| 36 | 6-Cl | $CH_3$ | H | (3-Methylthienyl)-2-methyl | 124 |
| 37 | 6-Cl | $CH_3$ | H | Thienyl-2-methyl | 121–123 |
| 38 | 6-Cl | $CH_3$ | H | $CH_2CH$=CH—$C_6H_5$ | 59 |
| 39 | 6-Cl | $CH_2SCH_3$ | H | $CH_2C_6H_4$-2-Cl | 128 |
| 40 | 6-Cl | $CH_2SCH_3$ | H | $CH_2C_6H_4$-2-$NO_2$ | 134 |
| 41 | 6-Cl | $CH_2SCH_3$ | H | 2-Picolyl | Oil |
| 42 | 6-Cl | $CH_2SCH_3$ | H | $CH_2C_6H_3$-2,4-$Cl_2$ | 143 |
| 43 | 6-Cl | $CH_2S$—i.Pr | H | $CH_2C_6H_3$-2,4-$Cl_2$ | Oil |
| 44 | 6-Cl | $CH_2S$—Bn | H | $CH_2C_6H_3$-2,4-$Cl_2$ | Oil |
| 45 | 6-Cl | $CH_2$—S—H | H | $CH_2C_6H_3$-2,4-$Cl_2$ | |
| 46 | 6-Cl | $C_2H_5$ | H | 2-Picolyl | 160–162 |
| 47 | 6-Cl | $CH_3$ | H | (6-$CH_3$)2—Picolyl | 158 |

Key:
$C_5H_{11}$ = 3-methyl-1-butyl
c-$C_4H_7$= cyclobutyl
c-$C_5H_9$ = cyclopentyl

EXAMPLE XXXIV (3RS)-3-Methyl-4-N-(3-oxo-1-butyl)-3,4-dihydroquinoxalin-2(1H)-one 3-Methyl-3,4-dihydroquinoxalin-2(1H)-one (0.5 g, 3.1 mmol) together with 0.35 ml (4.3 mmol) of methyl vinyl ketone and a catalytic amount of triethylamine were stirred for 20 hours at room temperature in 20 ml of anhydrous ethanol. Silica gel chromatography with methyl tert.-butyl ether/heptane=2:1 gave 620 mg (87%) of the desired product, melting point 108–109° C. (methyl tert.-butyl ether/heptane).

$^1$H NMR (270 MHz, $d_6$-DMSO): δ=1.03 (d, J=7 Hz, 3 H), 2.11 (s, 3H), 2.77 (t, J=6 Hz, 2 H), 3.30 (m, 1 H), 3.50 (m, 1 H), 3.88 (q, J=7 Hz, 1 H), 6.68 (m, 1 H), 6.78 (m, 1 H), 6.88 (m, 1 H), 10.31 ppm (br. s, 1 H). MS: (M+H)⁺=233, M⁺=232.

EXAMPLE XXXV (3S)-6-Chloro-4-N-chlorocarbonyl-3-methyl-3,4-dihydroquinoxalin-2(1H)-one The compound of Example IB (2.0 g, 0.01 mol) in 100 ml of anhydrous toluene was heated with bis-(trichloromethyl) carbonate (triphosgene) (1.5 g, 0.005 mol) for 1 hour at 80° C. in the presence of 2 ml (0.014 mol) of triethylamine. After cooling, the mixture was washed with water and saturated aqueous sodium chloride solution and dried (magnesium sulfate), and the solvent was removed under reduced pressure. The residue (2.5 g) crystallized after stirring with heptane, its purity being sufficient for preparative purposes. A sample of analytical purity was obtained by silica gel chromatography using ethyl acetate/heptane=1:1 as eluent. Melting point 142–144° C. ice-cooling, and the mixture was stirred for 1 hour at room temperature. 0.5 g (1.9 mmol) of the compound of Example XXXV were introduced, again with ice-cooling, and stirring was then continued for 2 hours at room temperature. For working-up, the mixture was treated with saturated aqueous sodium chloride solution, extracted twice with ethyl acetate and dried (sodium sulfate), and the solvent was stripped off. The solid residue was recrystallized from heptane/isopropanol, 0.35 g (35%), melting point 194–195° C.

$^1$H NMR (200 MHz, $d_6$-DMSO): δ=1.10 (d, J=7 Hz, 3 H), 4.93 (q, J=7 Hz, 1 H), 7.08 (d, J=9 Hz, 1 H), 7.33 (dd, J=9, 3 Hz, 1 H), 7.4–78.6 (m, 5 H), 7.78 (d, J=3 Hz, 1 H), 10.16 ppm (br. s, 1 H). MS: (M+H)⁺=333, (M-$C_6H_5$SH+H)⁺223.

The following compounds of the formula I were synthesized in analogous manner.

TABLE 11

| Nr. | R¹ₙ | R³ | R⁴ | R⁵ | M.P. ° C. |
|---|---|---|---|---|---|
| 1 | 6-Cl | $CH_3$ | H | $COOCH_2CH$=$CHCH_3$ | 116–117 |
| 2 | 6-Cl | $CH_3$ | H | $COOCH_2$=$C(CH_3)_2$ | 87–89 |
| 3 | 6-Cl | $CH_3$ | H | $COOCH_2C$≡CH | 147 |
| 4 | 6-Cl | $CH_3$ | H | $COOCH_2C$≡$CCH_3$ | 135 |
| 5 | 6-Cl | $CH_3$ | H | $COSCH_2C_6H_5$ | 158 |
| 6 | 6-Cl | $CH_3$ | H | $COSCH_2CH$=$CH_2$ | Oil |
| 7 | 6-Cl | $CH_3$ | H | $COOCH_2C(CH_3)$=$CH_2$ | 125–127 |
| 8 | 6-Cl | $CH_3$ | H | $COOC(CH_3)_3$ | |
| 9 | 6-Cl | $CH_3$ | H | COO-Cyclohex-2-en-1-yl | |
| 10 | 6-Cl | $CH_3$ | H | $COOCH(CH_2OCH(CH_3)_2)_2$ | Oil |
| 11 | 6-Cl | $CH_3$ | H | $COOCH(CH_3)_2$ | 141–142 |
| 12 | 6-Cl | $CH_3$ | H | $COOC_2H_4N(CH_3)_2$ | Oil |
| 13 | 6-Cl | $CH_3$ | H | $COOC_2H_4SCH_3$ | 108–110 |
| 14 | 6-Cl | $CH_3$ | H | $COSC_6H_5$ | 194–195 |
| 15 | 6-Cl | $CH_3$ | H | $COOCH_2C_6H_4$-2-$NO_2$ | 227–231 |
| 16 | 6-Cl | $CH_3$ | H | $COOCH_2C_6H_4$-3-$NO_2$ | 183–185 |
| 17 | 6-Cl | $CH_3$ | H | $COOCH_2C_6H_4$-4-Cl | 177–180 |
| 18 | 6-Cl | $CH_3$ | H | $COOCH_2C_6H_4$-2-Cl | 164 |
| 19 | 6-Cl | $CH_3$ | H | $COOCH_2CH$=$CHCH_2CH_3$ | Oil |
| 20 | 6-Cl | $CH_3$ | H | COO(3-Picolyl) | 160–161 |
| 21 | 6-Cl | $CH_3$ | H | COO(2-Picolyl) | 114–116 |
| 22 | 6-Cl | $CH_3$ | H | $COOCH_2C_6H_4$-4-$NO_2$ | 230–233 |
| 23 | 6-Cl | $CH_3$ | H | $COOCH_2CH_2C(CH_3)$=$CH_2$ | Oil |
| 24 | 6-Cl | $CH_3$ | H | CO-(4-Methylpiperazin-1-yl) | Oil |
| 25 | 6-Cl | $CH_3$ | H | CO-N$(CH_2)_5$ | 218–220 |
| 26 | 6-Cl | $CH_3$ | H | CO-N$(CH_2)_4$ | 200–203 |

TABLE 11-continued

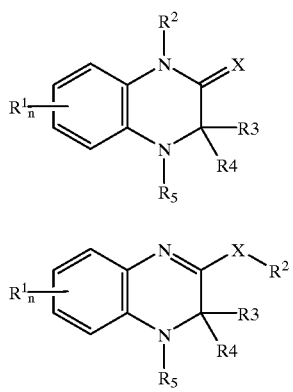

| Nr. | $R^1_n$ | $R^3$ | $R^4$ | $R^5$ | M.P. ° C. |
|---|---|---|---|---|---|
| 27 | 6-Cl | $CH_3$ | H | CO-Morpholin-1-yl | 193–195 |
| 28 | 6-Cl | $CH_3$ | H | $CO-HNCH_2Ph$ | 94–96 |
| 29 | 6-Cl | $CH_3$ | H | Cyclopropyl-methyloxy-carbonyl | 119–122 |

What is claimed is:

1. A compound of the formulae 1 or 1a (I)

(Ia)

or a physiologically acceptable salt thereof, wherein the substituents in the formulae 1 and 1a have the following meanings:

n is zero, one or two, the individual substituents $R^1$ independently of one another are fluorine, chlorine, bromine, trifluoromethyl, hydroxyl, $C_1-C_4$-alkyl, $C_1-C_4$-alkoxy, $(C_1-C_4$-alkoxy$)-(C_1-C_2$-alkoxy), $C_1-C_4$-alkylthio, nitro, amino, $C_1-C_4$-alkylamino, di$(C_1-C_4$-alkyl)amino, piperidino, morpholino, 1-pyrrolidinyl, 4-methylpiperazinyl, $C_1-C_4$-acyl, $C_1-C_4$-acyloxy, $C_1-C_4$-acylamino, cyano, carbamoyl, carboxyl, $(C_1-C_4$-alkyl)oxycarbonyl, hydroxysulfonyl or sulfamoyl, or a phenyl, phenoxy, phenylthio, phenylsulfonyl, phenoxysulfonyl, benzoyl, 2-pyridyl, 3-pyridyl or 4-pyridyl radical which is in each case substituted by up to two radicals $R^6$ which are independent of one another, where $R^6$ is fluorine, chlorine, bromine, cyano, trifluoromethyl, nitro, amino, $C_1-C_4$-alkyl, $C_1-C_4$-alkoxy, $(C_1-C_4$-alkyl)oxycarbonyl, phenyl or phenoxy, $R^2$ is hydrogen and $R^5$ is $C_1-C_6$-alkyl, optionally substituted by $C_1-C_4$-alkoxy or $C_1-C_4$-alkylthio;

$C_2-C_6$-alkenyl, optionally substituted by oxo;

$C_3-C_6$-allenyl;

$C_3-C_8$-alkynyl;

$C_3-C_6$-cycloalkyl;

$C_5-C_6$-cycloalkenyl;

$(C_3-C_6$-cycloalkyl)-$(C_1-C_2$-alkyl), optionally substituted by $C_1-C_4$-alkyl;

$(C_3-C_6$-cycloalkenyl)-$(C_1-C_2$-alkyl);

$C_1-C_6$-alkylcarbonyl, optionally substituted by hydroxyl, $C_1-C_4$-alkoxy, $C_1-C_4$-alkylamino, $C_1-C_4$-alkenylamino, di$(C_1-C_4$-alkyl)amino, 1-pyrrolidinyl, piperidino, morpholino, 4-methylpiperazin-1-yl or $C_1-C_4$-alkylthio;

$C_2-C_6$-alkenylcarbonyl;

$C_1-C_6$-alkyloxycarbonyl, optionally substituted by fluorine, chlorine, bromine, hydroxyl, $C_1-C_4$-alkoxy, $C_1-C_4$-alkylamino, di$(C_1-C_4$-alkyl)amino or $C_1-C_4$-alkylthio;

$C_2-C_6$-alkenyloxycarbonyl;

$C_2-C_6$-alkynyloxycarbonyl;

$C_1-C_6$-alkylthiocarbonyl;

$C_2-C_6$-alkenylthiocarbonyl;

$C_1-C_6$-alkylamino- or di$(C_1-C_6$-alkyl)aminocarbonyl;

pyrrolidin-1-yl, morpholino-, piperidino-, piperazinyl-, or 4-methylpiperazin-1-ylcarbonyl;

$C_2-C_6$-alkenylamino- or di$(C_1-C_6$-alkenyl)aminocarbonyl;

$C_1-C_4$-alkylsulfonyl;

$C_1-C_4$-alkenylsulfonyl;

or aryl, arylcarbonyl, (arylthio)carbonyl, aryloxycarbonyl, arylaminocarbonyl, (arylamino)thiocarbonyl, arylalkylaminocarbonyl, arylsulfonyl, arylalkyl, arylalkenyl, arylalkoxycarbonyl or aryl(alkylthio)carbonyl, each of which is substituted by up to two radicals $R^6$ which are independent of one another, it being possible for the aryl radical to have in each case 6 to 10 carbon atoms, for the alkenyl radical to have 2 to 8 carbon atoms, for the alkyl radical to have in each case 1 to 3 carbon atoms and $R^6$ being as defined above, or 2-, 3- or 4-picolyl, 2- or 3-furylmethyl, 2- or 3-thienylmethyl, 2- or 3-pyrrolylmethyl, or 2-, 3- or 4-pyridylcarbonyl, each of which is substituted by up to two radicals $R^6$ which are independent of one another, and $R^3$ and $R^4$ are identical or different and independently of one another are hydrogen, $C_2-C_4$-alkyl, optionally substituted by hydroxyl, mercapto, $C_1-C_4$-alkoxy, $C_1-C_4$-alkylthio, $C_1-C_4$-alkylsulfonyl, $C_1-C_4$-alkylsulfinyl, carboxyl or carbamoyl;

$C_2-C_6$-alkenyl, aryl, benzyl, thienyl or thienylmethyl, each of which is substituted by up to two radicals $R^6$ which are independent of one another, $R^6$ having the meaning as defined above, $R^3$ and $R^4$ together can also be part of a saturated or unsaturated carbocyclic ring which has 3 to 8 carbon atoms and can optionally be substituted in each case by oxo or thioxo, and X is oxygen or sulfur, with the exception of: those compounds in which $R^3$ and $R^4$ are both hydrogen; and those compounds of the formula 1 in which $R^3$ and $R^4$ are identical but are not hydrogen, $R^1$ is 7-methyl, 7-methoxy, or hydrogen, and $R^5$ is benzoyl or phenylsulfonyl, wherein the benzoyl or phenylsulfonyl radical is substituted by up to two radicals $R^6$ which are independent of one another.

2. A compound of the formula 1 or 1a as claimed in claim 1 wherein $R^5$ is 2-butynyl, cyclopropylmethyl optionally substituted by $C_1-C_4$-alkyl, cyclohexenylmethyl, vinyloxycarbonyl, allyloxycarbonyl, isopropenyloxycarbonyl, butenyloxycarbonyl, pentenyloxycarbonyl, propynyloxycarbonyl, butynyloxycarbonyl, allylthiocarbonyl, substituted phenyl or substituted benzoyl.

3. The compound according to claim 1, wherein $R^3$ or $R^4$ is ethyl.

4. A compound of the formulae 1 or 1a

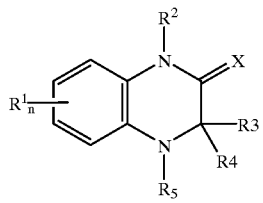 (I)

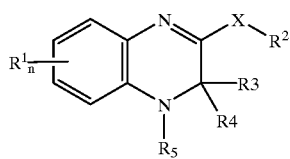 (Ia)

or a physiologically acceptable salt thereof, wherein the substituents in the formulae 1 and 1a have the following meanings:

n is zero or one;

the individual substituents $R^1$ independently of one another are fluorine, chlorine, bromine, $C_1$–$C_4$-alkyl, $C_1$–$C_2$-alkoxy, $C_2$–$C_4$-acyl, or cyano;

$R^2$ is hydrogen and $R^5$ is $C_2$–$C_6$-alkenyl;
$C_3$–$C_8$-alkynyl;
$(C_3$–$C_6$-cycloalkyl)-$(C_1$–$C_2$-alkyl), optionally substituted by $C_1$–$C_4$-alkyl;
$(C_3$–$C_6$-cycloalkenyl)-$(C_1$–$C_2$-alkyl);
$C_2$–$C_6$-alkylcarbonyl;
$C_2$–$C_6$-alkenylcarbonyl;
$C_1$–$C_6$-alkyloxycarbonyl;
$C_2$–$C_6$-alkenyloxycarbonyl;
$C_2$–$C_6$-alkynyloxycarbonyl;
$C_2$–$C_6$-alkenylthiocarbonyl;
$C_1$–$C_4$-alkylsulfonyl;
$C_1$–$C_4$-alkenylsulfonyl;

or aryl, arylalkyl or arylalkenyl, each of which is substituted by up to two radicals $R^6$ which are independent of one another, it being possible for the aryl radical to have in each case 1 to 3 carbon atoms, for the alkenyl radical to have 2 to 2 carbon atoms;

or 1-naphthylmethyl, 2- or 3-picolyl, 2-furylmethyl, or 2- or 3-thienylmethyl, each of which is substituted by up to two radicals $R^6$ which are independent of one another, where $R^6$ is fluorine, chlorine, bromine, cyano, $C_1$–$C_2$-alkyl, or C1–C2-alkoxy; and $R^3$ and $R^4$ are identical or different and independently of one another are hydrogen, $C_2$–$C_4$-alkyl, optionally substituted by hydroxyl, mercapto, $C_1$–$C_4$-alkoxy, or $C_1$–$C_4$-alkylthio; and X is oxygen or sulfur, with the exception of those compounds in which $R^3$ and $R^4$ are both hydrogen.

5. A compound of the formula 1 or 1a as claimed in claim 4 wherein $R^5$ is 2-butynyl, cyclopropylmethyl, vinyloxycarbonyl, butenyloxycarbonyl, pentenyloxycarbonyl, propynyloxycarbonyl, butynyloxycarbonyl, alkylthiocarbonyl, or aryl substituted by up to two radicals $R^6$.

6. A pharmaceutical composition comprising an effective amount of at least one compound of the formula 1a as claimed in claim 1 together with a pharmaceutically acceptable excipient.

* * * * *

UNITED STATES PATENT AND TRADEMARK OFFICE
CERTIFICATE OF CORRECTION

PATENT NO.     : 6,369,057 B1
DATED          : April 9, 2002
INVENTOR(S)    : Uta-Maria Billhardt et al.

It is certified that error appears in the above-identified patent and that said Letters Patent is hereby corrected as shown below:

<u>Column 60,</u>
Line 12, "2 to 2" should read -- 2 to 3 --.
Line 20, "C1-C2-alkoxy" should read -- $C_1$-$C_2$-alkoxy --.

Signed and Sealed this

Eighth Day of October, 2002

*Attest:*

JAMES E. ROGAN
*Attesting Officer*   *Director of the United States Patent and Trademark Office*